(12) United States Patent
Vallapureddy et al.

(10) Patent No.: US 7,610,065 B2
(45) Date of Patent: Oct. 27, 2009

(54) METHOD AND APPARATUS FOR ANTENNA SELECTION IN A DIVERSITY ANTENNA SYSTEM FOR COMMUNICATING WITH IMPLANTABLE MEDICAL DEVICE

(75) Inventors: Vineel Vallapureddy, St. Paul, MN (US); Earle Roberts, Maple Grove, MN (US); Joseph E. Bange, Eagan, MN (US); Jeffrey A. Von Arx, Minneapolis, MN (US); Prashant Rawat, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 533 days.

(21) Appl. No.: 11/068,478

(22) Filed: Feb. 28, 2005

(65) Prior Publication Data

US 2006/0194615 A1    Aug. 31, 2006

(51) Int. Cl.
*H04M 1/00* (2006.01)
(52) U.S. Cl. ............... 455/562.1; 455/561; 455/550.1; 455/73
(58) Field of Classification Search ............... 455/73, 455/550.1, 561, 562.1, 101, 91, 25, 7, 9, 455/11.1, 8, 17; 607/1, 2, 60, 9, 32; 375/267
See application file for complete search history.

(56) References Cited

U.S. PATENT DOCUMENTS

| 4,958,645 | A | | 9/1990 | Cadell et al. |
| 5,142,534 | A | | 8/1992 | Simpson et al. |
| 5,342,408 | A | | 8/1994 | deCoriolis et al. |
| 5,787,122 | A | | 7/1998 | Suzuki |
| 6,167,312 | A | * | 12/2000 | Goedeke ............... 607/60 |
| 6,169,925 | B1 | * | 1/2001 | Villaseca et al. ......... 607/60 |
| 6,226,508 | B1 | | 5/2001 | Takahashi et al. |

(Continued)

FOREIGN PATENT DOCUMENTS

EP    0744841 A2    11/1996

(Continued)

OTHER PUBLICATIONS

"U.S. Appl. No. 11/068,476 Response filed Jan. 11, 2007 to Non-Final Office Action mailed Oct. 16, 2007", 18 pgs.

(Continued)

*Primary Examiner*—Walter Benson
*Assistant Examiner*—David S Luo
(74) *Attorney, Agent, or Firm*—Schwegman, Lundberg & Woessner, P.A.

(57) ABSTRACT

A far-field radio frequency telemetry (RF) system for communicating with an implantable medical device includes a diversity antenna system. An antenna control circuit selects one or more antennas of the diversity antenna system for reducing potential data transmission errors associated with nulls encountered by the telemetry system due to environmental reflections of RF electromagnetic waves. In one embodiment, a different active antenna is selected when a transmission failure deemed to be associated with a null is detected. In another embodiment, a new antenna is selected on a regular basis to reduce the probability of encountering a null. In another embodiment, the telemetry system includes multiple processing paths each associated with one antenna of the diversity antenna system, and a different processing path is selected when the transmission failure deemed to be associated with a null is detected.

32 Claims, 12 Drawing Sheets

U.S. PATENT DOCUMENTS

| | | | |
|---|---|---|---|
| 6,434,429 | B1 | 8/2002 | Kraus et al. |
| 6,488,704 | B1 * | 12/2002 | Connelly et al. ........... 623/1.15 |
| 6,574,510 | B2 | 6/2003 | Von Arx et al. |
| 6,716,165 | B1 * | 4/2004 | Flanders et al. ............. 600/301 |
| 6,844,854 | B2 * | 1/2005 | Johnson et al. ............. 343/702 |
| 6,889,086 | B2 | 5/2005 | Mass et al. |
| 6,985,088 | B2 | 1/2006 | Goetz et al. |
| 7,069,086 | B2 | 6/2006 | Von Arx |
| 7,072,718 | B2 * | 7/2006 | Von Arx et al. ............... 607/60 |
| 7,107,085 | B2 * | 9/2006 | Doi ........................ 455/575.7 |
| 2003/0114897 | A1 | 6/2003 | Von Arx et al. |
| 2003/0174069 | A1 | 9/2003 | Goetz et al. |
| 2004/0106967 | A1 * | 6/2004 | Von Arx et al. ............... 607/60 |
| 2004/0212496 | A1 | 10/2004 | Villaseca et al. |
| 2004/0260363 | A1 | 12/2004 | Arx et al. |
| 2005/0222629 | A1 | 10/2005 | Perschbacher et al. |
| 2005/0283208 | A1 | 12/2005 | Von Arx et al. |
| 2006/0009818 | A1 | 1/2006 | Von Arx et al. |
| 2006/0030903 | A1 | 2/2006 | Seeberger et al. |
| 2006/0111643 | A1 | 5/2006 | Cazares et al. |
| 2006/0161223 | A1 | 7/2006 | Vallapureddy et al. |
| 2006/0195161 | A1 | 8/2006 | Li |
| 2006/0195162 | A1 | 8/2006 | Arx et al. |
| 2007/0260293 | A1 | 11/2007 | Carpenter et al. |

FOREIGN PATENT DOCUMENTS

| | | | |
|---|---|---|---|
| EP | 0808033 | A2 | 11/1997 |
| EP | 0863620 | A2 | 9/1998 |
| EP | 0889603 | A2 | 1/1999 |
| WO | WO-2005115541 | A1 | 12/2005 |
| WO | WO-2006093766 | A1 | 9/2006 |
| WO | WO-2006093964 | A1 | 9/2006 |

OTHER PUBLICATIONS

"U.S. Appl. No. 11/068,476 Response filed Nov. 16, 2007 to Non-Final Office Action mailed Aug. 16, 2007", 13 pages.

"Non-Final Office Action mailed Oct. 16, 2006 in U.S. Appl. No. 11/068,476", 9 pgs.

"Non-Final Office Action Mailed Aug. 16, 2007 in U.S. Appl. No. 11/068,476", 9 pgs.

Guidant, "Feature Sheet and Specifications: Zoom Latitude", *Doc. No. C3-194-1005*, (2005),2 pgs.

Guidant, "Go Beyond the Wand", *Doc. No. C3-107-0505*, (2005),2 pgs.

Guidant, "Think Beyond the Wand", *Doc. No. C3-101-0505*, (2005),3 pgs.

Guidant, "What if you could ZIP through implants and follow ups?", *Doc. No. C3-117-0505*, (2005),2 pgs.

Guidant, "What if your patient develops diaphragmatic stimulation?", *Doc. No. C3-116-0505*, (2005),2 pgs.

Harney, Austin, et al., "Wireless Short-Range Devices: Designing a Global License-Free System for Frequencies <1 GHz", *Analog Dialogue 40-03*, (Mar. 2006), 1 pg.

Zarlink Semiconductor, "Medical Implantable RF Transceiver", (2005),40 pgs.

* cited by examiner

US 7,610,065 B2

METHOD AND APPARATUS FOR ANTENNA SELECTION IN A DIVERSITY ANTENNA SYSTEM FOR COMMUNICATING WITH IMPLANTABLE MEDICAL DEVICE

CROSS-REFERENCE TO RELATED APPLICATION

This application is related to co-pending, commonly assigned, U.S. patent application Ser. No. 11/068,497, entitled "DIVERSITY ANTENNA SYSTEM FOR COMMUNICATION WITH AN IMPLANTABLE MEDICAL DEVICE," filed on Feb. 28, 2005 and U.S. patent application Ser. No. 11/068,476, entitled "METHOD AND APPARATUS FOR OPERATING A DIVERSITY ANTENNA SYSTEM COMMUNICATING WITH IMPLANTABLE MEDICAL DEVICE" filed on Feb. 28, 2005, which are hereby incorporated by reference in their entirety.

TECHNICAL FIELD

This document relates generally to telemetry for implantable medical systems and particularly to an external telemetry system having diversity antennas for communicating with an implantable medical device.

BACKGROUND

Medical devices are implanted in human bodies for monitoring physiological conditions, diagnosing diseases, treating diseases, or restoring functions of organs or tissues. Examples of such implantable medical devices include cardiac rhythm management (CRM) devices, neural stimulators, neuromuscular stimulators, drug delivery devices, and biological therapy devices. When an implantable medical device is intended for long-term use in a patient, its size and power consumption are limited by implantability and longevity requirements. Consequently, many implantable medical devices depend on external systems to perform certain functions. Communication between an implantable method device and an external system is performed via telemetry. Examples of specific telemetry functions include programming the implantable medical device to perform certain monitoring or therapeutic tasks, extracting an operational status of the implantable medical device, transmitting real-time physiological data acquired by the implantable medical device, and extracting physiological data acquired by and stored in the implantable medical device.

One type of telemetry between the implantable medical device and the external system is based on inductive coupling between two closely-placed coils using the mutual inductance between these coils. One of the coils is part of the implantable medical device, and the other coil is part of the external system. This type of telemetry is referred to as inductive telemetry or near-field telemetry because the coils must be closely situated for obtaining magnetically coupled communication.

Far-field radio-frequency (RF) telemetry provides another means for communications between the implantable medical device and the external system. The far-field RF telemetry is performed using an RF transceiver in the implantable medical device and an RF transceiver in the external system. The far-field RF telemetry frees the patient from any body surface attachment that limits mobility and is more suitable for use when the patient is at home, without the attendance by the physician or other professional caregiver.

The far-field RF telemetry between the implantable medical device and the external system often operates in an environment where RF electromagnetic waves are reflected from various kinds of surfaces. Destructive interference between the incident and reflective waves results in nulls, where the incident wave and reflected wave cancel out. The far-filed RF telemetry link is substantially interrupted when an antenna encounters a null. While such a null is moving and usually transient, the interruption to the telemetry link may last long enough to cause a data transmission error.

Therefore, there is a need for ensuring the quality of far-field RF telemetry between an external system and an implanted device when nulls are present.

SUMMARY

A far-field RF telemetry system for communicating with an implantable medical device includes a diversity antenna system. An antenna control circuit selects one or more antennas of the diversity antenna system for reducing potential data transmission errors associated with nulls.

In one embodiment, an external system communicating with an implantable medical device includes a diversity antenna system, a transceiver, an antenna interface circuit, and an antenna control circuit. The diversity antenna system includes a plurality of antennas for transmitting an outgoing signal to the implantable medical device and receiving an incoming signal from the implantable medical device. The transceiver transmits outgoing data frames by modulating the outgoing signal and receives incoming data frames by demodulating the incoming signal. The antenna interface circuit includes a switch circuit that connects an antenna of the diversity antenna system to the transceiver according to an antenna selection signal. The antenna control circuit produces the antenna selection signal and includes a fading detector, an antenna selector, and an antenna switching timing circuit. The fading detector detects a transmission failure deemed to be associated with a null. The antenna selector adjusts the antenna selection signal for connecting a different antenna of the diversity antenna system to the transceiver in response to a detection of the transmission failure. The antenna switching timing circuit holds the antenna selection signal while a frame of the outgoing data frames is being transmitted or a frame of the incoming data frames is being received.

In one embodiment, a method is provided for operating a telemetry system communicating with an implantable medical device. Using a diversity antenna system including a plurality of antennas, an outgoing signal modulated by outgoing data frames is transmitted to the implantable medical device, and an incoming signal modulated by incoming data frames is received from the implantable medical device. An active antenna is selected from the diversity antenna system according to an antenna selection signal. A transmission failure deemed to be associated with a null is detected. In response to a detection of the transmission failure, the antenna selection signal is adjusted for selecting a different active antenna of the diversity antenna system. The antenna selection signal is held while a frame of the outgoing data frames is being transmitted or a frame of the incoming data frames is being received. When no data frame is being transmitted or received, the different active antenna is selected from the diversity antenna system according to the adjusted antenna selection signal.

In one embodiment, a telemetry system for communicating with an implantable medical device includes a diversity antenna system, a transceiver, an antenna interface circuit, and an antenna control circuit. The diversity antenna system includes a plurality of antennas for transmitting an outgoing signal to the implantable medical device and receiving an incoming signal from the implantable medical device. The transceiver transmits outgoing data frames by modulating the outgoing signal and receives incoming data frames by demodulating the incoming signal. The antenna interface circuit includes a switch circuit that connects an antenna of the diversity antenna system to the transceiver according to an antenna selection signal. The antenna control circuit includes a selection sequence generator that produces the antenna selection signal for selecting an antenna of the diversity antenna system to be connected to the transceiver in response to an antenna switching timing signal.

In one embodiment, a method is provided for operating a telemetry system communicating with an implantable medical device. Using a diversity antenna system including a plurality of antennas, an outgoing signal modulated by outgoing data frames is transmitted to the implantable medical device, and an incoming signal modulated by incoming data frames is received from the implantable medical device. An active antenna is selected from the diversity antenna system according to an antenna selection signal. The antenna selection signal is produced for selecting a new active antenna of the diversity antenna system on a predetermined periodic basis.

In one embodiment, an external system communicating with an implantable medical device includes a diversity antenna system, an external system controller, a transceiver, and an antenna control circuit. The diversity antenna system includes a plurality of antennas for transmitting an outgoing signal to the implantable medical device and receiving an incoming signal from the implantable medical device. The transceiver transmits outgoing data frames by modulating the outgoing signal and receives incoming data frames by demodulating the incoming signal. The transceiver includes a plurality of receiving modules and a switch circuit. The receiving modules each have an input coupled to an antenna of the diversity antenna system and an output. The switch circuit connects the output of one of the receiving modules to the external system controller according to a receiving path selection signal. The antenna control circuit produces the receiving path selection signal and includes a signal quality assessment circuit and a receiving path selector. The signal quality assessment circuit produces an indication of quality for the incoming signal processed by each of the receiving modules. The receiving path selector adjusts the receiving path selection signal based on the indications of quality for the incoming signal produced for the plurality of receiving modules.

In one embodiment, a method is provided for operating a telemetry system communicating with an implantable medical device. Using a diversity antenna system including a plurality of antennas, an outgoing signal modulated by outgoing data frames is transmitted to the implantable medical device, and an incoming signal modulated by incoming data frames is received from the implantable medical device. The incoming signal is processed through a plurality of processing paths each coupled to an antenna of the diversity antenna system. An indication of quality is produced for the incoming signal processed by each of the processing paths. One of the processing paths is selected based on the detected indications of quality associated with the processing paths.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

In the drawings, which are not necessarily drawn to scale, like numerals describe similar components throughout the several views. The drawings illustrate generally, by way of example, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses an RF telemetry system for bi-directional communication between an implantable medical device and an external system. The external system includes an external telemetry system that uses a diversity antenna system and an antenna control circuit to selecting one or more active antenna of the diversity antenna system for reducing or minimizing data transmission errors associated with nulls. An active antenna is an antenna that is currently used to transmit and/or receive signals. In one embodiment, a different active antenna is selected when a transmission failure such as a data transmission error or a sudden signal strength drop is detected. Such a transmission failure is deemed to be associated with a null resulting from destructive interference between the incident and reflected electromagnetic waves. A null is a point where the destructive interference causes a substantial loss of the RF telemetry including interruption of data communication. In another embodiment, a new antenna is selected to be the active antenna on a regular basis, such as on a periodic basis. This reduces the probability for a currently active antenna to encounter a null. In another embodiment, the telemetry system includes multiple processing paths each associated with an antenna of the diversity antenna system. A different processing path is selected when the transmission failure is detected.

Figure 1:
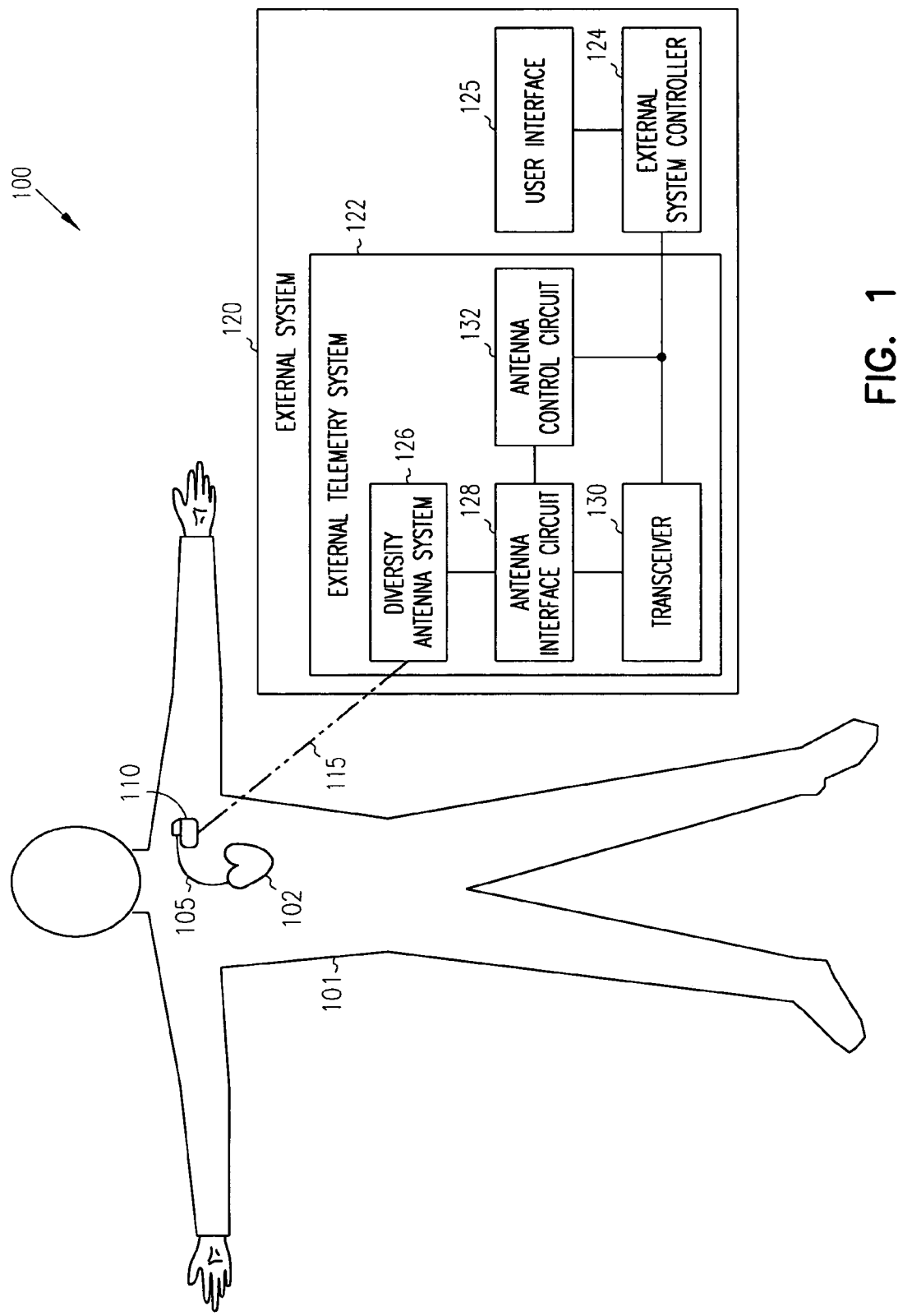
FIG. 1 is an illustration of an embodiment of a CRM system including an implantable medical device and an external system and portions of an environment in which the CRM system is used.

FIG. 1 is an illustration of an embodiment of portions of a CRM system 100 and portions of an environment in which system 100 is used. System 100 includes an implantable medical device 110 and an external system 120. In the illustrated embodiment, after being implanted into a patient's body 101, implantable medical device 110 is coupled to the patient's heart 102 through a lead system 105. Examples of implantable medical device 110 include pacemakers, cardioverter/defibrillators, cardiac resynchronization therapy (CRT) devices, cardiac remodeling control therapy (RCT) devices, neural stimulators, drug delivery systems, biological therapy devices, and patient monitoring devices. External system 120 allows a physician or other caregiver to interact with implantable medical device 110 through an RF telemetry link 115, which provides for bi-directional data communication between implantable medical device 110 and external system 120.

RF telemetry link 115 provides for data transmission from implantable medical device 110 to external system 120. This includes, for example, transmitting real-time physiological data acquired by implantable medical device 110, extracting physiological data acquired by and stored in implantable medical device 110, extracting therapy history data stored in implantable medical device 110, and extracting data indicating an operational status of implantable medical device 110 (e.g., battery status and lead impedance). RF telemetry link 115 also provides for data transmission from external system 120 to implantable medical device 110. This includes, for example, programming implantable medical device 110 to acquire physiological data, programming implantable medical device 110 to perform at least one self-diagnostic test (such as for a device operational status), and programming implantable medical device 110 to deliver at least one therapy.

RF telemetry link 115 is a far-field telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one embodiment, a communication range of RF telemetry link 115 (a distance over which data is capable of being wirelessly communicated) is at least ten feet but can be as long as allowed by the communication technology utilized. Unlike an inductive telemetry link using a coil placed near implantable medical device 110, attached to the patient, and electrically connected to external system 120 with a cable, using RF telemetry link 115 frees the patient from any physical restraints caused by the coil and the cable and allows external system 120 to be placed entirely away from the sterile filed during an operation such as the implantation of implantable medical device 110.

Telemetry link 115 is supported by an implant telemetry system of implantable medical device 110 and an external telemetry system 122 of external system 120. External telemetry system 122 includes a diversity antenna system 126, an antenna interface circuit 128, a transceiver 130, and an antenna control circuit 132. Diversity antenna system 126 includes a plurality of antennas to transmit an outgoing signal to implantable medical device 110 and to receive an incoming signal from implantable medical device 110. Antenna interface circuit 128 includes tuning circuitry for diversity antenna system 126 and routes the outgoing and incoming signals between diversity antenna system 126 and transceiver 130. Transceiver 130 transmits outgoing data frames by modulating the outgoing signal and receives incoming data frames by demodulating the incoming signal. The outgoing data frames and the incoming data frames are each a frame being a logic unit of data including a header, a payload, and a trailer. The header includes a "comma," which includes a unique set of bits for signaling a receipt of a frame. A lack of comma, or failure to receive the comma, indicates a failure to receive a frame. The payload includes the data block being transmitted. The trailer includes a cyclic redundancy check (CRC) character having a value generated by a transmitter. A receiver receives that CRC character and also recalculates the CRC character based on the received data block and compares the result to the received CRC character in the trailer. The data is deemed to be correctly transmitted if the recalculated CRC character matches the received CRC character. A CRC error refers to a mismatch between the recalculated CRC character and the received CRC character. Depending on the specific communication formats, the header and the trailer each include additional information for flagging, control of data recovery, and/or synchronization of the receiving device. Antenna control circuit 132 controls the operation of antenna interface circuit for an approximately optimal performance, or at least an acceptable performance, of diversity antenna system 126. In one embodiment, antenna control circuit 132 selects an active antenna of diversity antenna system 126 or a processing path associated with an antenna of diversity antenna system 126 based on the quality of the outgoing signal and/or the incoming signal. Such quality is measured by, for example, strength of signal and/or integrity of the data frames. In a further embodiment, antenna control circuit 132 selects a different active antenna of diversity antenna system 126 or a different processing path associated with an antenna of diversity antenna system 126 in response to the detection of a transmission failure, such as a sudden drop in signal strength or a data transmission error. Such a transmission failure is deemed to be associated with a null. In another further embodiment, antenna control circuit selects a new active antenna of diversity antenna system 126 or a new processing path associated with an antenna of diversity antenna system 126 on a periodic basis to reduce the probability for diversity antenna system 126 to encounter a null. External telemetry system 122 is connected to an external system controller 124, which allows external system 120 to receive information acquired by implantable medical device 110 and to control the operation of implantable medical device 110. External system controller 124 receives the incoming data frames from transceiver 130 and sends the outgoing data frames to transceiver 130. A user interface 125 allows the physician or other caregiver to view the received information and to enter commands and parameters to control the operation of CRM system 100.

In one embodiment, external system 120 includes a programmer. In another embodiment, as illustrated in FIG. 2, external system 120 includes a patient management system.

Figure 2:
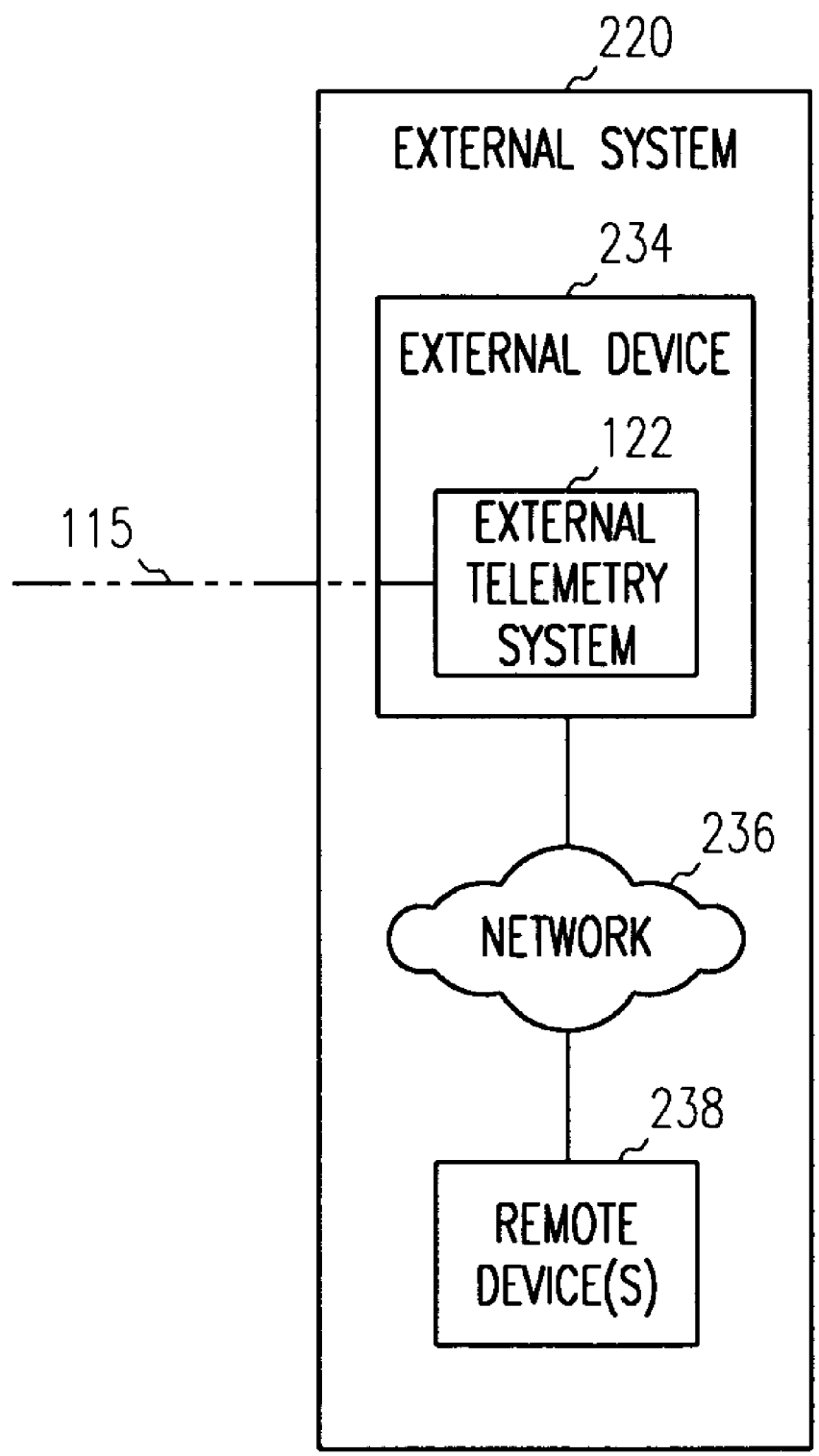
FIG. 2 is a block diagram illustrating a specific embodiment of the external system.

FIG. 2 is a block diagram illustrating an embodiment of external system 220, which is a specific embodiment of external system 120. As illustrated in FIG. 2, external system 220 is a patient management system including an external device 234, a telecommunication network 236, and one or more remote devices 238. External device 234 is placed within the vicinity of implantable medical device 110 and includes external telemetry system 122 to communicate with implantable medical device 110 via telemetry link 115. Remote device(s) 238 are in one or more remote locations and communicates with external device 234 through network 236, thus allowing a physician or other caregiver to monitor and treat a patient from a distant location and/or allowing access to various treatment resources from the one or more remote locations.

Figure 3:
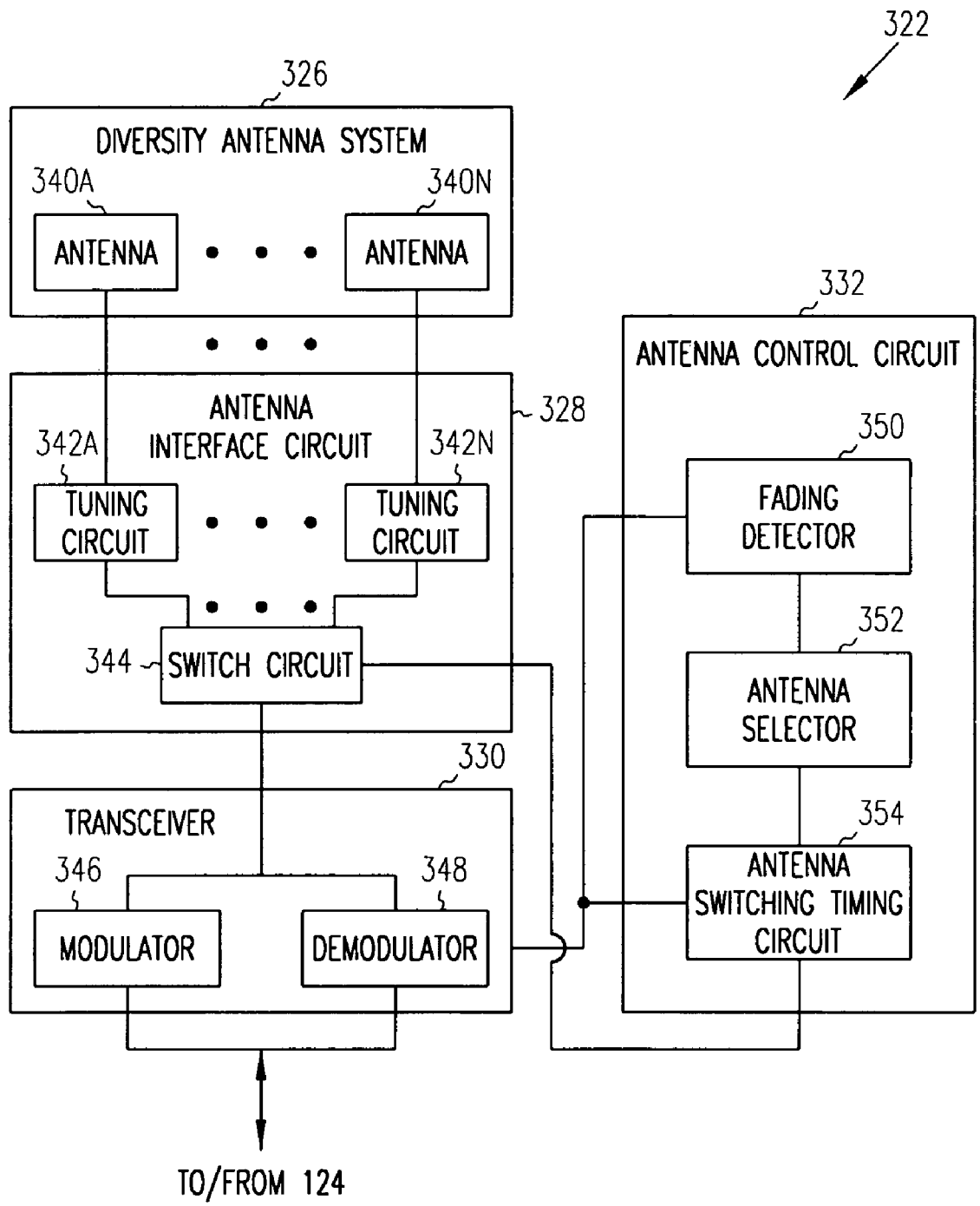
FIG. 3 is a block diagram illustrating an embodiment of a telemetry system of the external system.

FIG. 3 is a block diagram illustrating an embodiment of an external telemetry system 322, which is a specific embodiment of external telemetry system 122. External telemetry system 322 includes a diversity antenna system 326, an antenna interface circuit 328, a transceiver 330, and an antenna control circuit 332.

Diversity antenna system 326 is a specific embodiment of diversity antenna system 126 and includes two or more antennas 340A-N. Each of antennas 340A-N allows for transmitting an outgoing signal to implantable medical device 110 and/or receiving an incoming signal from implantable medical device 110. In one embodiment, diversity antenna system 126 includes two antennas. In one specific embodiment, the two antennas are mounted onto a chassis of an external device such as the programmer or external device 234. In other embodiments, diversity antenna system 126 includes three or more antennas. One example of diversity antenna system 126 is discussed in U.S. patent application Ser. No. 11/068,497, entitled "DIVERSITY ANTENNA SYSTEM FOR COMMUNICATION WITH AN IMPLANTABLE MEDICAL DEVICE," filed on Feb. 28, 2005, which is incorporated by reference herein in its entirety.

Antenna interface circuit 328 is a specific embodiment of antenna interface circuit 128 and includes tuning circuits 342A-N and a switch circuit 344. Tuning circuits 342A-N each provide tuning for a corresponding antenna of antennas 342A-N. Switch circuit 344 provides for a controllable connection between an antenna of diversity antenna system 326 and transceiver 330 according to an antenna selection signal. In one embodiment, switch circuit 344 substantially completes the change of the connection from between an antenna of diversity antenna system 326 and transceiver 330 to between another antenna of diversity antenna system 326 and transceiver 330 in about 50 microseconds to 1 millisecond.

Transceiver 330 is a specific embodiment of transceiver 130 and includes a modulator 346 and a demodulator 348. Modulator 346 produces the outgoing signal by modulating an RF carrier with the outgoing data frames. In one embodiment, the frequency of the RF carrier for the outgoing signal is in a range of approximately 902 MHz to 928 MHz, with approximately 914 MHz being one specific example. The data transmission rate for the outgoing signal is in a range of approximately 60 kilobits per second to 500 kilobits per second, with approximately 204.8 kilobits per second being one specific example. Demodulator 348 recovers the incoming data frames by demodulating the received incoming signal.

The implant telemetry circuit of implantable medical device 110 produces the incoming signal by modulating another RF carrier with the incoming data frames. In one embodiment, the frequency of the RF carrier for the incoming signal is in a range of approximately 902 MHz to 928 MHz, with approximately 914 MHz being one specific example. The data transmission rate for the incoming signal is in a range of approximately 60 kilobits per second to 500 kilobits per second, with approximately 102.4 kilobits per second being one specific example. In one embodiment, amplitude-shift-keying (ASK) is the modulation scheme used for both the outgoing signal and the incoming signal. Modulator 346 is an ASK modulator, and demodulator 348 is an ASK demodulator.

Antenna control circuit 332 is a specific embodiment of antenna control circuit 132 and includes a fading detector 350, an antenna selector 352, and an antenna switching timing circuit 354. Fading detector 350 detects a transmission failure deemed to be associated with a null. Exemplary specific embodiments of fading detector 350 are discussed below with reference to FIGS. 4-8. Antenna selector 352 adjusts the antenna selection signal for connecting a different antenna of diversity antenna system 326 to transceiver 330 in response to a detection of the transmission failure. Antenna switching timing circuit 354 holds the antenna selection signal while a frame of the outgoing data frames is being transmitted or a frame of the incoming data frames is being received. Thus, after antenna selector 352 adjusts the antenna selection signal, the change of connection between diversity antenna system 326 and transceiver 330 occurs when no data frame is being transmitted or received. This prevents a potential data transmission error from being resulted from the change of connection, i.e., switching from one antenna to another. In one embodiment, antenna switching timing circuit 354 delays the adjustment of the antenna selection signal by antenna selector 352 until an ongoing transmission or reception of a data frame is completed. In another embodiment, antenna switching timing circuit 354 keeps the adjusted antenna selection signal from being applied to switch circuit 344 until an ongoing transmission or reception of a data frame is completed. In one embodiment, antenna switching timing circuit 354 holds the antenna selection signal while a data frame is being transmitted or received only if the switching time of switch circuit 344 for switching from one antenna to another is not substantially higher than the time required for transmitting one data bit. In another embodiment, external telemetry system 322 includes an error protection circuit to prevent data transmission errors caused by an operation of switching circuit 344 in response to a change in the antenna selection signal. The error protection circuit corrects a detected error in received incoming data frames by executing an error correction algorithm.

Figure 4:
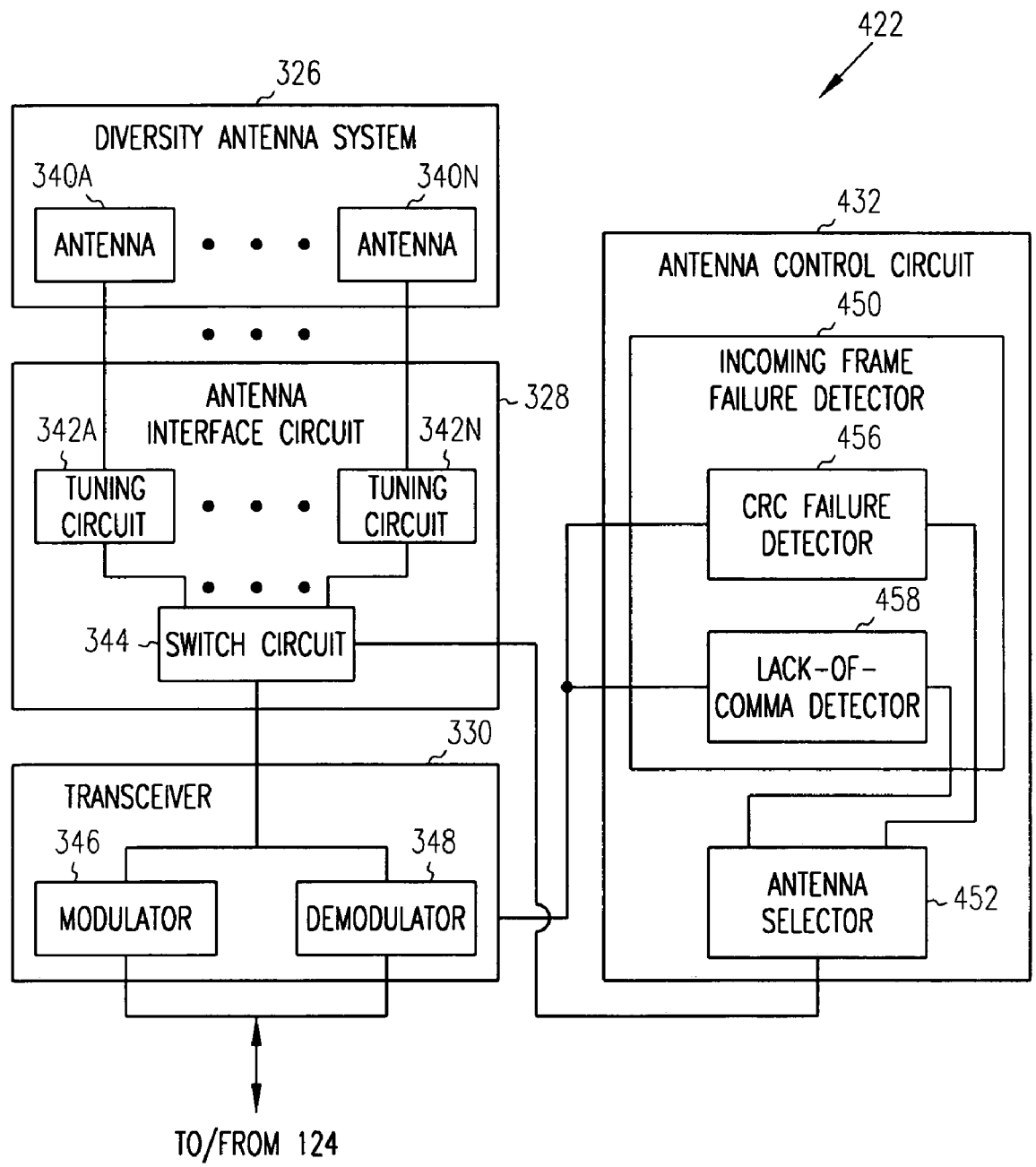
FIG. 4 is a block diagram illustrating a specific embodiment of the telemetry system of FIG. 3.

FIG. 4 is a block diagram illustrating an embodiment of an external telemetry system 422, which is a specific embodiment of external telemetry system 322. External telemetry system 422 includes diversity antenna system 326, antenna interface circuit 328, transceiver 330, and an antenna control circuit 432.

Antenna control circuit 432 is a specific embodiment of antenna control circuit 332 and includes an incoming frame failure detector 450 and an antenna selector 452. Incoming frame failure detector 450 is a specific embodiment of fading detector 350 and detects an incoming frame failure as the transmission failure from the incoming signal. The incoming frame failure includes a data transmission error in at least one of the incoming data frames. In one embodiment, a single data transmission error in one incoming data frame constitutes the transmission failure deemed to be associated with a null.

Incoming frame failure detector 450 includes a CRC failure detector 456 and/or a lack-of-comma detector 458. CRC failure detector 456 detects a CRC failure from the incoming signal and indicates the incoming frame failure if the CRC failure is detected. Lack-of-comma detector 458 detects a comma indicative of a receipt of an incoming data frame during a predetermined time window and indicates the incoming frame failure if the comma is not detected during the predetermined time window. In other embodiments, incoming frame failure detector 450 includes one or more error detector detecting data transmission errors of types other than the CRC failure and the lack of comma. Generally, incoming frame failure detector 450 detects any predetermined type data transmission error in at least one of the incoming data frames and indicates the incoming frame failure when the predetermined type data transmission error is detected.

Antenna selector 452 is a specific embodiment of antenna selector 352 and adjusts the antenna selection signal for connecting a different antenna of diversity antenna system 326 to transceiver 330 when the incoming frame failure is indicated by incoming frame failure detector 450. In one embodiment, antenna selector 452 adjusts the antenna selection signal in response to the detection of either a CRC failure or a lack of comma. In response to the adjusted antenna selection signal, switch circuit 344 connects the different antenna to transceiver 330 for receiving the incoming signal and transmitting the outgoing signal until the detection of another incoming frame failure is indicated.

Figure 5:
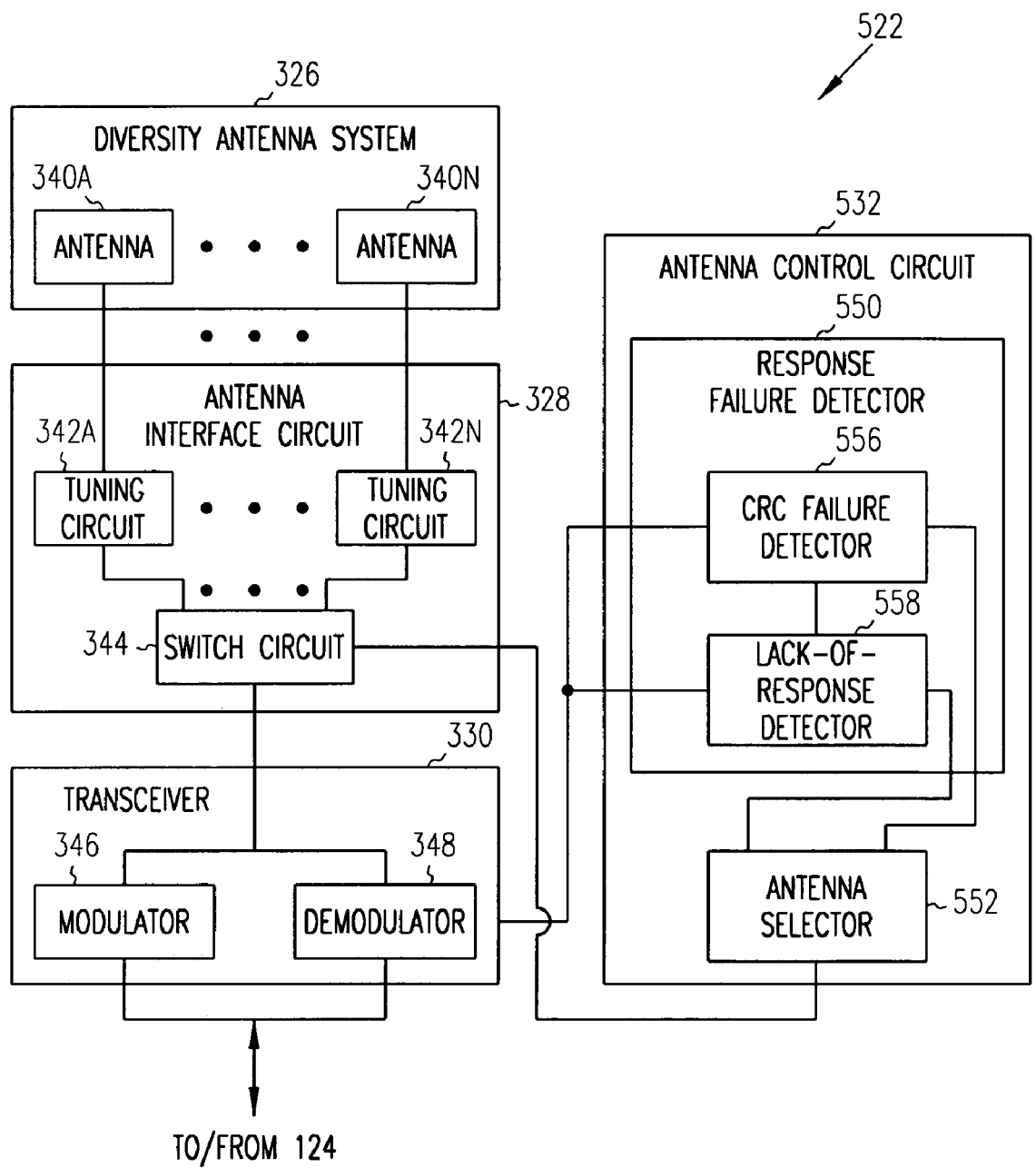
FIG. 5 is a block diagram illustrating another specific embodiment of the telemetry system of FIG. 3.

FIG. 5 is a block diagram an embodiment of an external telemetry system 522, which is another specific embodiment of external telemetry system 322. External telemetry system 522 includes diversity antenna system 326, antenna interface circuit 328, transceiver 330, and an antenna control circuit 532.

Antenna control circuit 532 is a specific embodiment of antenna control circuit 332 and includes a response failure detector 550 and an antenna selector 552. Response failure detector 550 is a specific embodiment of fading detector 350 and detects a response failure as the transmission failure from the incoming signal. The response failure includes a data transmission error in at least one response frame of the incoming data frames. The response frame is an incoming data frame produced and sent by implantable medical device 110 in response to an outgoing data frame transmitted to implantable medical device 110. In one embodiment, a single data transmission error in one response frame constitutes the transmission failure deemed to be associated with a null. Response failure detector 550 includes a CRC failure detector 556 and/or a lack-of-response detector 558. CRC failure detector 556 detects a CRC failure from the incoming signal and indicates the response failure if the CRC failure is detected. Lack-of-response detector 558 detects a response frame indicative of a receipt of the outgoing data frame transmitted to implantable medical device 110 and indicates the response failure if no response frame is detected during a predetermined time window starting from the transmission of the outgoing data frame.

Antenna selector 552 is a specific embodiment of antenna selector 352 and adjusts the antenna selection signal for connecting a different antenna of diversity antenna system 326 to transceiver 330 when the response failure is indicated. In one embodiment, antenna selector 552 adjusts the antenna selection signal in response to the detection of either a CRC failure or a lack of response. In response to the adjusted antenna selection signal, switch circuit 344 connects the different antenna to transceiver 330 for receiving the incoming signal and transmitting the outgoing signal until the detection of another response failure is indicated.

Figure 6:
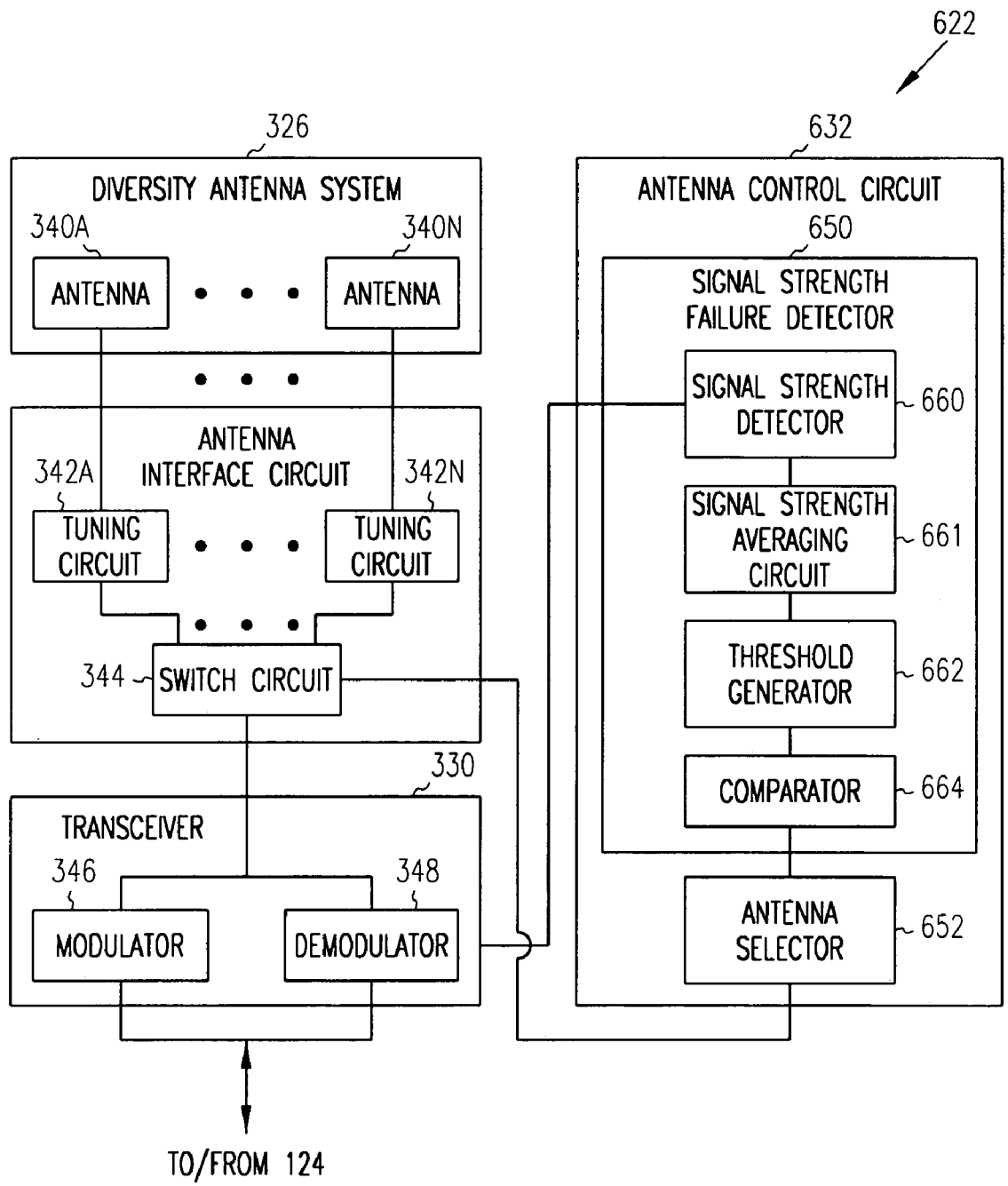
FIG. 6 is a block diagram illustrating another specific embodiment of the telemetry system of FIG. 3.

FIG. 6 is a block diagram illustrating an embodiment of an external telemetry system 622, which is another specific embodiment of external telemetry system 322. External telemetry system 622 includes diversity antenna system 326, antenna interface circuit 328, transceiver 330, and an antenna control circuit 632.

Antenna control circuit 632 is a specific embodiment of antenna control circuit 332 and includes a signal strength failure detector 650 and an antenna selector 652. Signal strength failure detector 650 is a specific embodiment of fading detector 350 and detects a signal strength failure as the transmission failure from the incoming signal. The signal strength failure as detected by signal strength failure detector 650 is deemed to be caused by a null. Signal strength failure detector 650 includes a signal strength detector 660, a signal strength averaging circuit 661, a threshold generator 662, and a comparator 664. Signal strength detector 660 measures a strength parameter being a measure of the strength of the incoming signal. In one embodiment, the strength parameter is a power measured in dBm (decibel ratio (log 10) of watts (W) to one milliwatt (1 mW)), and signal strength detector 660 includes a signal power detector. In another embodiment, the strength parameter is an amplitude measured in volts, and signal strength detector 660 includes a signal amplitude detector. Signal strength averaging circuit 661 calculates an average value for the measured strength parameter. In one embodiment, signal strength averaging circuit 661 calculates the average value for the strength parameter over a predetermined period of time. In another embodiment, signal strength averaging circuit 661 calculates an average value for the strength parameter over a predetermined number of frames. In a specific embodiment, the predetermined number is in a range of 4 to 50 frames, with approximately 6 frames being a specific example. Threshold generator 662 dynamically produces a threshold strength based on the average value for the measured strength parameter. In one embodiment, the threshold strength is produced by subtracting a predetermined margin from the average value for the measured strength parameter. In one specific embodiment, the predetermined margin is in a range of approximately 10 dBm to 30 dBm, with approximately 20 dBm being a specific example. Comparator 664 includes an input to receive the average value for the measured strength parameter, another input to receive the dynamically produced threshold strength, and an output indicative of the signal strength failure when the average value for the measured strength parameter falls below the dynamically produced threshold strength.

Antenna selector 652 is a specific embodiment of antenna selector 352 and adjusts the antenna selection signal for connecting a different antenna of diversity antenna system 326 to transceiver 330 when comparator 664 indicates the signal strength failure. In one embodiment, antenna selector 652 adjusts the antenna selection signal immediately in response to an indication of the signal strength failure. In another embodiment, antenna selector 652 adjusts the antenna selection signal if the signal strength failure is indicated for a predetermined time interval in a range of approximately 20 milliseconds to 200 milliseconds, with approximately 50 milliseconds being a specific example. In response to the adjusted antenna selection signal, switch circuit 344 connects the different antenna to transceiver 330 for receiving the incoming signal and transmitting the outgoing signal until the detection of another signal strength failure is indicated.

Figure 7:
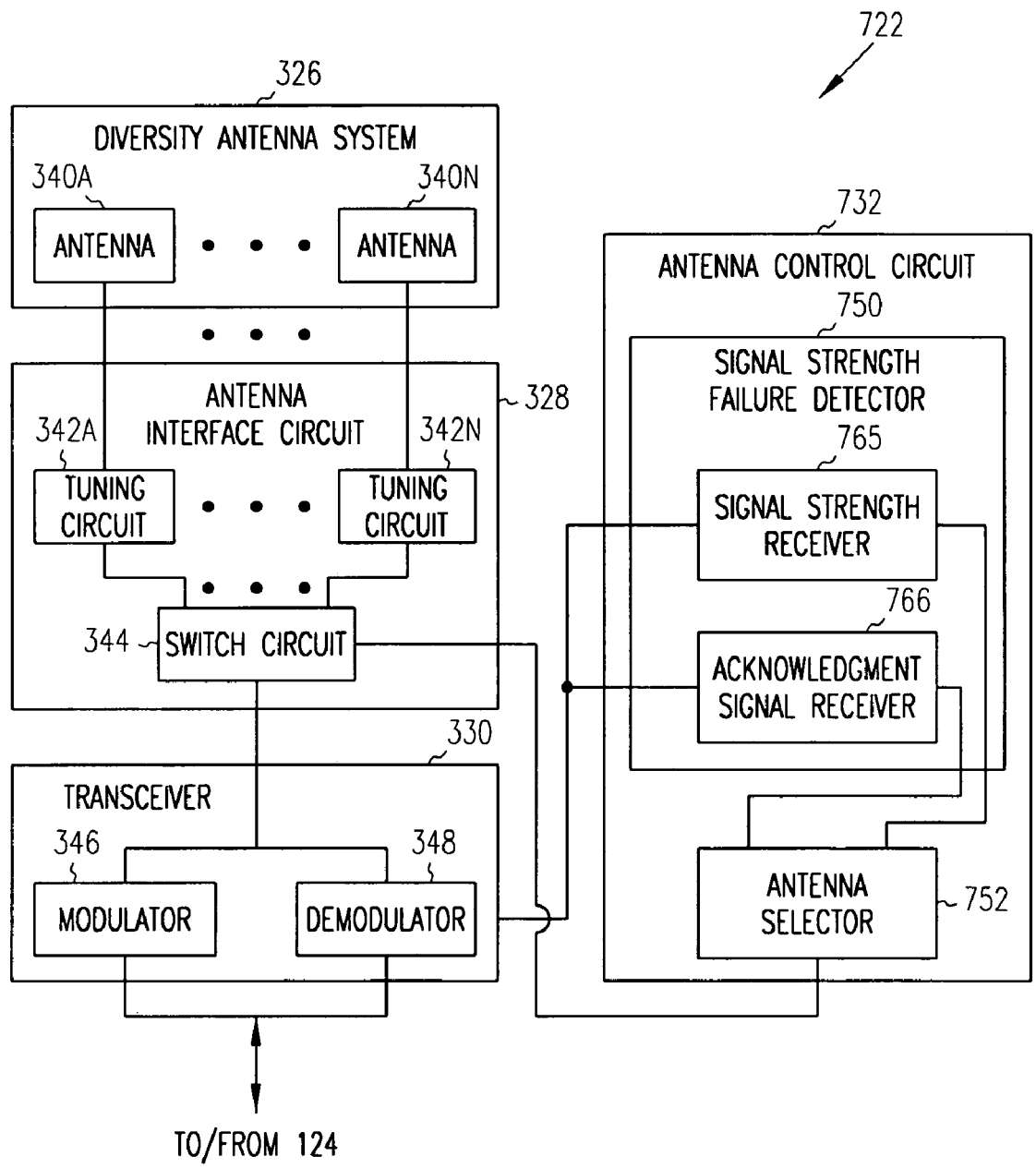
FIG. 7 is a block diagram illustrating another specific embodiment of the telemetry system of FIG. 3.

FIG. 7 is a block diagram illustrating an embodiment of an external telemetry system 722, which is another specific embodiment of external telemetry system 322. External telemetry system 722 includes diversity antenna system 326, antenna interface circuit 328, transceiver 330, and an antenna control circuit 732.

Antenna control circuit 732 is a specific embodiment of antenna control circuit 332 and includes a signal strength failure detector 750 and an antenna selector 752. Signal strength failure detector 750 is another specific embodiment of fading detector 350 and detects a signal strength failure associated with the outgoing signal as the transmission failure. Signal strength failure detector 750 includes a signal strength receiver 765 and/or an acknowledgement signal receiver 766. Signal strength receiver 765 receives a reporting frame being an incoming data frame produced and sent by implantable medical device 110, which detects the signal strength failure in receiving the outgoing frames. Signal strength receiver 765 indicates the signal strength failure when the reporting frame includes data indicating a signal strength failure associated with the outgoing signal. Acknowledgement signal receiver 766 receives an acknowledgement frame of the incoming data frames and indicates the signal strength failure if the acknowledgement frame is not received within a predetermined time interval after a transmission of an outgoing frame to implantable medical device 110. The acknowledgement frame is indicative of a successful receipt of the outgoing frame by implantable medical device 110.

Antenna selector 752 is a specific embodiment of antenna selector 352 and adjusts the antenna selection signal for connecting a different antenna of diversity antenna system 326 to transceiver 330 when the signal strength failure is indicated. In one embodiment, antenna selector 752 adjusts the antenna selection signal in response to either a receipt of a data frame indicative of a signal strength failure in outgoing signal as received by implantable medical device 110 or a lack of the acknowledgement frame. In response to the adjusted antenna selection signal, switch circuit 344 connects the different antenna to transceiver 330 for receiving the incoming signal and transmitting the outgoing signal until the detection of another signal strength failure is indicated.

Figure 8:
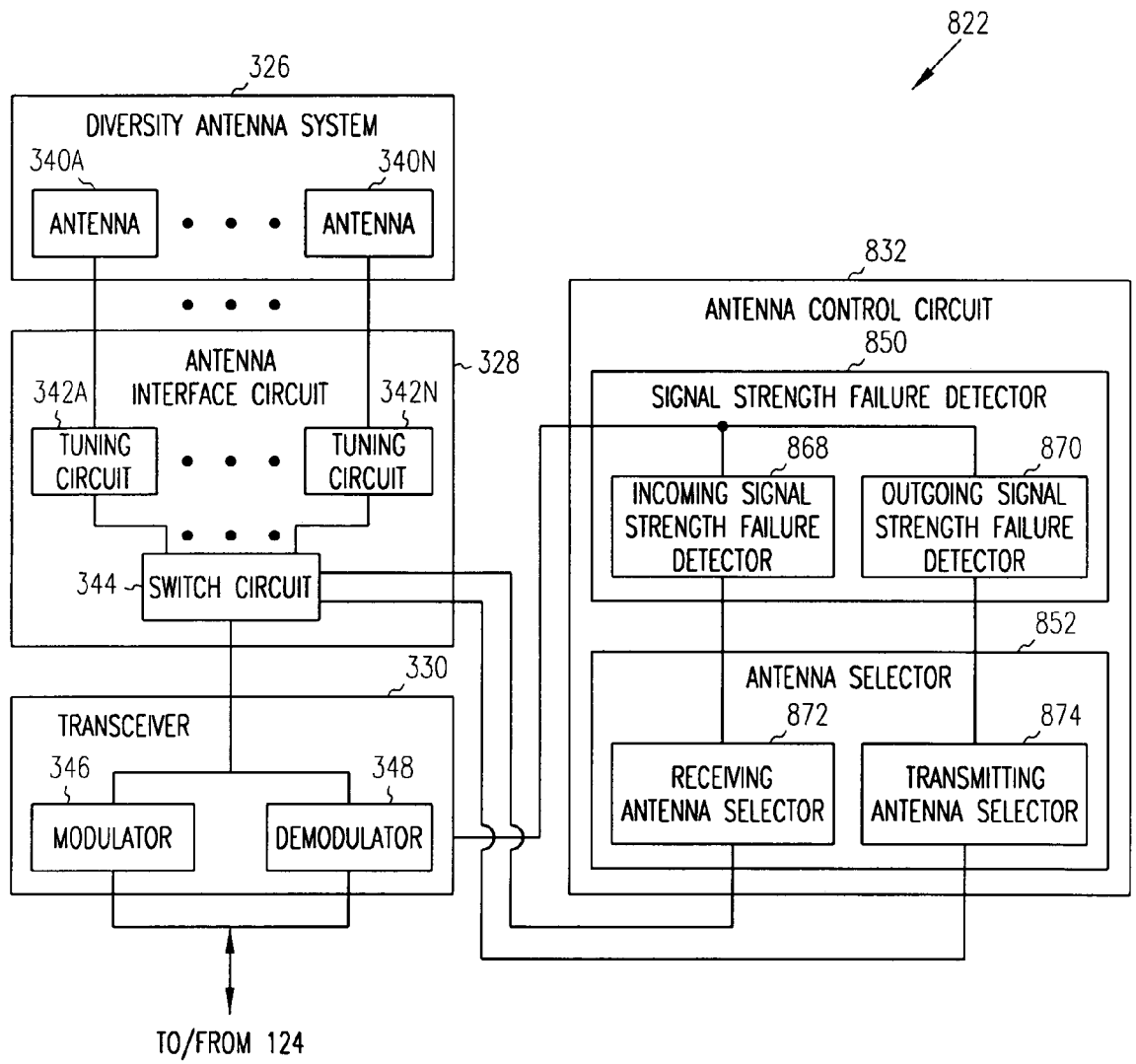
FIG. 8 is a block diagram illustrating another specific embodiment of the telemetry system of FIG. 3.

FIG. 8 is a block diagram an embodiment of an external telemetry system 822, which is another specific embodiment of external telemetry system 322. External telemetry system 822 includes diversity antenna system 326, antenna interface circuit 328, transceiver 330, and an antenna control circuit 832.

Antenna control circuit 832 is a specific embodiment of antenna control circuit 332 and includes a signal strength failure detector 850 and an antenna selector 852. Signal strength failure detector 850 is another specific embodiment of fading detector 350 and detects signal strength failures associated with the incoming signal and the outgoing signal. Signal strength failure detector 850 includes an incoming signal strength failure detector 868 and an outgoing signal strength failure detector 870. Incoming signal strength failure detector 868 detects a signal strength failure associated with the incoming signal as the transmission failure and indicates an incoming signal strength failure when the signal strength failure is detected. In one embodiment, incoming signal strength failure detector 868 is substantially identical or similar to signal strength failure detector 650. Outgoing signal strength failure detector 870 detects signal strength failures associated with the outgoing signal as the transmission failure and indicates an outgoing signal strength failure when the signal strength failure is detected. In one embodiment, outgoing signal strength failure detector 870 is substantially identical or similar to signal strength failure detector 750.

Antenna selector 852 includes a receiving antenna selector 872 and a transmitting antenna selector 874. Receiving antenna selector 872 adjusts the antenna selection signal for selecting a different antenna of diversity antenna system 326 for receiving the incoming signal when a detection of the incoming signal strength failure is indicated. Transmitting antenna selector 874 adjusts the antenna selection signal for selecting a different antenna of diversity antenna system 326 for transmitting the outgoing signal when a detection of the outgoing signal strength failure is indicated. In one embodiment, the antenna selection signal allows selection of two different antennas: one for receiving the incoming signal and the other for transmitting the outgoing signal. In another embodiment, the antenna selection signal allows selection of either one antenna, or two different antennas, for receiving the incoming signal and transmitting the outgoing signal.

In various other specific embodiments, fading detector 350 selectively includes one or more elements of incoming frame failure detector 450, response failure detector 550, signal strength failure detector 650, signal strength failure detector 750, and signal strength failure detector 850. In one exemplary embodiment, fading detector 350 includes incoming frame failure detector 450 (or portions thereof) and signal strength failure detector 650 (or portions thereof). Antenna selector 452 adjusts the antenna selection signal in response to the detection of either an incoming frame failure or a signal strength failure. In another embodiment, fading detector 350 includes incoming frame failure detector 450, response failure detector 550, and signal strength failure detector 850. Antenna selector 452 adjusts the antenna selection signal in response to the detection of any of an incoming frame failure, a response failure, an incoming signal strength failure, and an outgoing signal strength failure. Other embodiments involving such embodiments will become apparent to those skilled in the art upon reading and understanding this document.

Figure 9:
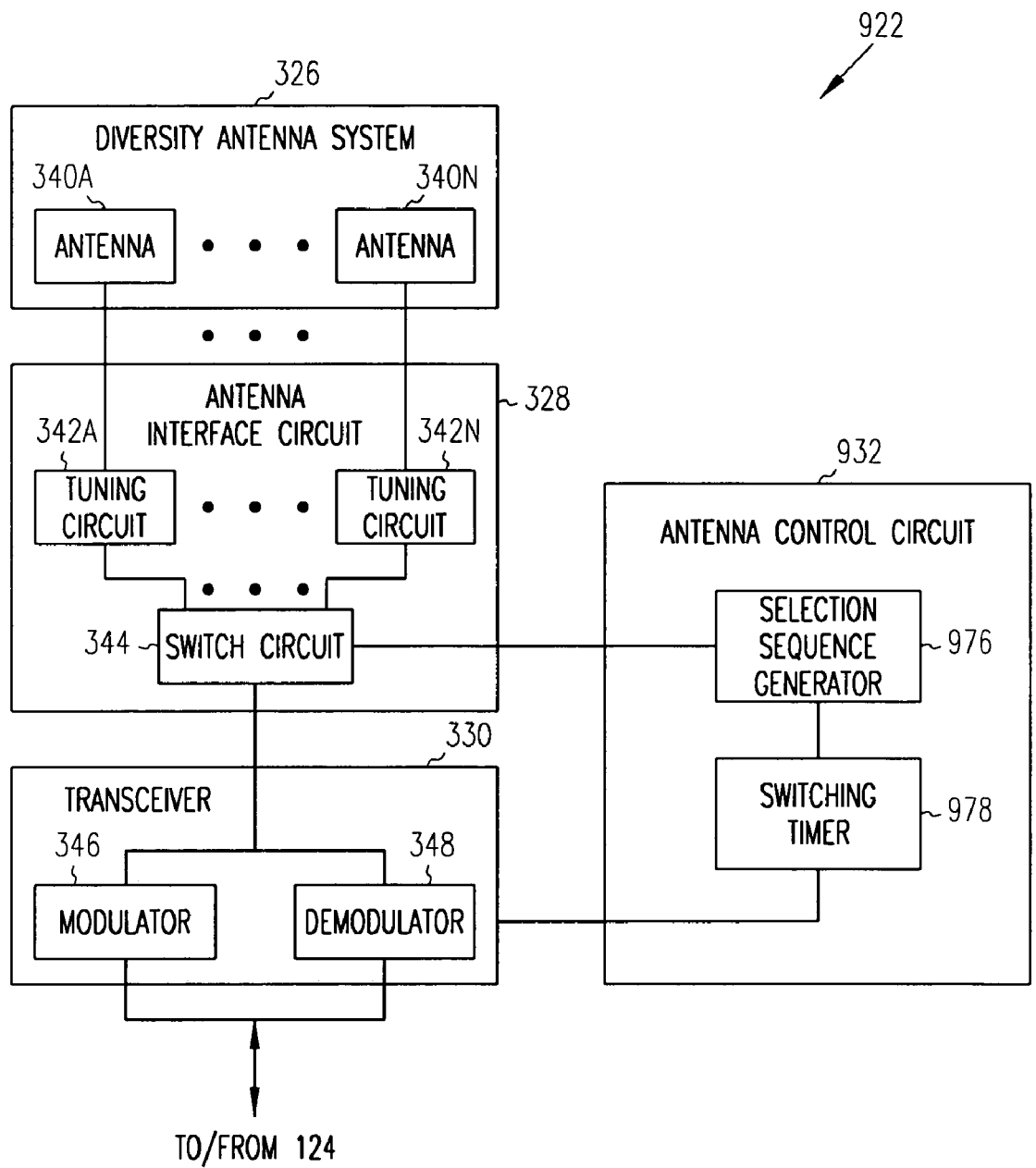
FIG. 9 is a block diagram illustrating another embodiment of the telemetry system of the external system.

FIG. 9 is a block diagram illustrating an embodiment of an external telemetry system 922, which is another specific embodiment of external telemetry system 122. External telemetry system 922 includes diversity antenna system 326, antenna interface circuit 328, transceiver 330, and an antenna control circuit 932.

Antenna control circuit 932 is another specific embodiment of antenna control circuit 132 and includes a selection sequence generator 976 and a switching timer 978. Selection sequence generator 976 produces the antenna selection signal for selecting an antenna of diversity antenna system 326 to be connected to transceiver 330 in response to an antenna switching timing signal. The antenna is used for receiving the incoming signal and transmitting the outgoing signal. In one embodiment, selection sequence generator 976 includes a random sequence generator that dynamically generates a random sequence and produces the antenna selection signal to select an antenna of diversity antenna system 326 in response to the antenna switching timing signal according to the dynamically generated random sequence. In another embodiment, selection sequence generator 976 includes a predetermined sequence generator that produces the antenna selection signal to select an antenna of diversity antenna system 326 in response to the antenna switching timing signal according to a predetermined sequence such as a built-in sequence or a programmed sequence. Switching timer 978 generates the antenna switching timing signal according to a predetermined schedule specifying times at which a new antenna is to be selected. In one embodiment, the predetermined schedule includes a predetermined period being in a range of approximately 50 milliseconds to 500 milliseconds, with approximately 200 milliseconds being a specific example. Switching timer 978 generates the antenna switching timing signal on a period basis using this predetermined period. In one embodiment, switching timer 978 also includes a switching holding circuit that holds the antenna switching timing signal while a frame of the outgoing data frames is being transmitted or a frame of the incoming data frames is being received. This prevents possible data transmission errors caused by switching from one antenna to another while a data frame is being received or transmitted. In one embodiment, switching timer 978 delays the generation of the antenna switching timing signal until an ongoing transmission or reception of a data frame is completed. In another embodiment, switching timer 978 keeps any change in the antenna selection signal from being applied to switch circuit 344 until an ongoing transmission or reception of a data frame is completed.

Figure 10:
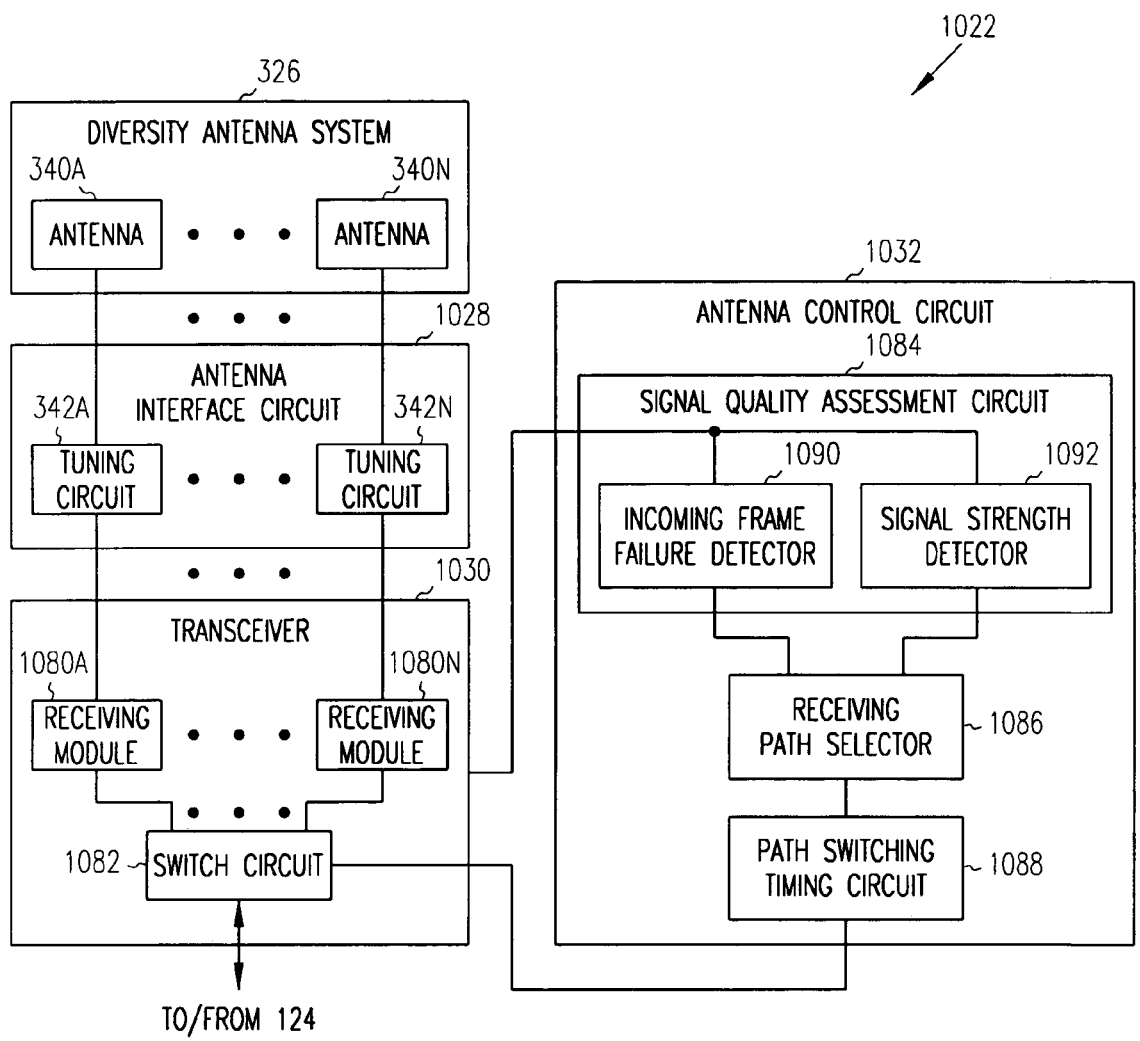
FIG. 10 is a block diagram illustrating another embodiment of the telemetry system of the external system.

FIG. 10 is a block diagram illustrating an embodiment of an external telemetry system 1022, which is another specific embodiment of external telemetry system 122. External telemetry system 1022 includes diversity antenna system 326, an antenna interface circuit 1028, a transceiver 1030, and an antenna control circuit 1032.

Antenna interface circuit 1028 is a specific embodiment of antenna interface circuit 128 and includes tuning circuits 342A-N. Tuning circuits 342A-N each provide tuning for a corresponding antenna of antennas 342A-N.

Transceiver 1030 is a specific embodiment of transceiver 130 and includes a plurality of receiving modules 1080A-N and a switch circuit 1082. Receiving modules 1080A-N each have an input coupled to a corresponding antenna of antennas 342A-N through a corresponding tuning circuit of tuning circuit 342A-N. Switch circuit 1082 connects the output of one receiving module of receiving modules 1080A-N to external system controller 124 according to a receiving path selection signal. That is, the incoming signal processed by one of receiving modules 1080A-N is selected for use by external system controller 124 according to the receiving path selection signal.

Antenna control circuit 1032 is a specific embodiment of antenna control circuit 132 and produces the receiving path selection signal. Instead of selecting one active antenna as in external telemetry systems 322-922, two or more of antennas 340A-N are active through a telemetry session. Antenna control circuit 1032 selects an effective antenna by selecting a receiving path including that antenna. Each receiving path includes an antenna of antennas 340A-N, a corresponding tuning circuit of tuning circuits 342A-N, and a corresponding receiving module of receiving modules 1080A-N. For example, one of the receiving paths includes antenna 340A, tuning circuit 342A, and receiving module 1080A. Selecting a receiving path includes connecting the output of one receiving module of receiving modules 1080A-N to external system controller 124. Antenna control circuit 1032 includes a signal quality assessment circuit 1084, a receiving path selector 1086, and a path switching timing circuit 1088.

Signal quality assessment circuit 1084 produces an indication of quality for the incoming signal processed by each of receiving modules 1080A-N. In the illustrated embodiment, signal quality assessment circuit 1084 includes an incoming frame failure detector 1090 and a signal strength detector 1092. Incoming frame failure detector 1090 detects incoming frame failures from the incoming signal processed by each of receiving modules 1080A-N. In one specific embodiment, incoming frame failure detector 1090 includes a CRC failure detector that detects a CRC failure from the incoming signal processed by each of receiving modules 1080A-N and indicates the incoming frame failure for any receiving module in which the CRC failure is detected. In another specific embodiment, incoming frame failure detector 1090 includes a lack-of-comma detector adapted to detect a comma indicative of a data frame from the incoming signal processed by each of receiving modules 1080A-N during a predetermined time window and indicates the incoming frame failure for any receiving module in which the comma is not detected. Signal strength detector 1092 measures a strength parameter being a measure of strength of the incoming signal processed by each of receiving modules 1080A-N. In one embodiment, signal strength detector 1092 includes an incoming signal strength failure detector that detects an incoming signal strength failure associated with the incoming signal processed by each of receiving modules 1080A-N. In a specific embodiment, the incoming signal strength failure detector is substantially identical to similar to signal strength failure detector 650.

Receiving path selector 1086 adjusts the receiving path selection signal based on the indications of quality for the incoming signal produced for receiving modules 1080A-N. The indications of quality include one or both of the incoming frame failure and the incoming signal strength failure. Receiving path selector 1086 adjusts the receiving path selection signal to deselect any of the receiving paths in which at least one of the incoming frame failure and the incoming signal strength failure is detected. In one embodiment, receiving path selector 1086 adjusts the receiving path selection signal based on the measured strength parameters for the receiving paths.

Path switching timing circuit 1088 holds the receiving path selection signal while a frame of the outgoing data frames is being transmitted or a frame of the incoming data frames is being received. This prevents possible data transmission error caused by switching from one receiving path to another while a data frame is being received or transmitted. In one embodiment, path switching timing circuit 1088 delays the adjustment of the receiving path selection signal until an ongoing transmission or reception of a data frame is completed. In another embodiment, path switching timing circuit 1088 keeps any change in the receiving path selection signal from being applied to switch circuit 1082 until an ongoing transmission or reception of a data frame is completed.

Figure 11:
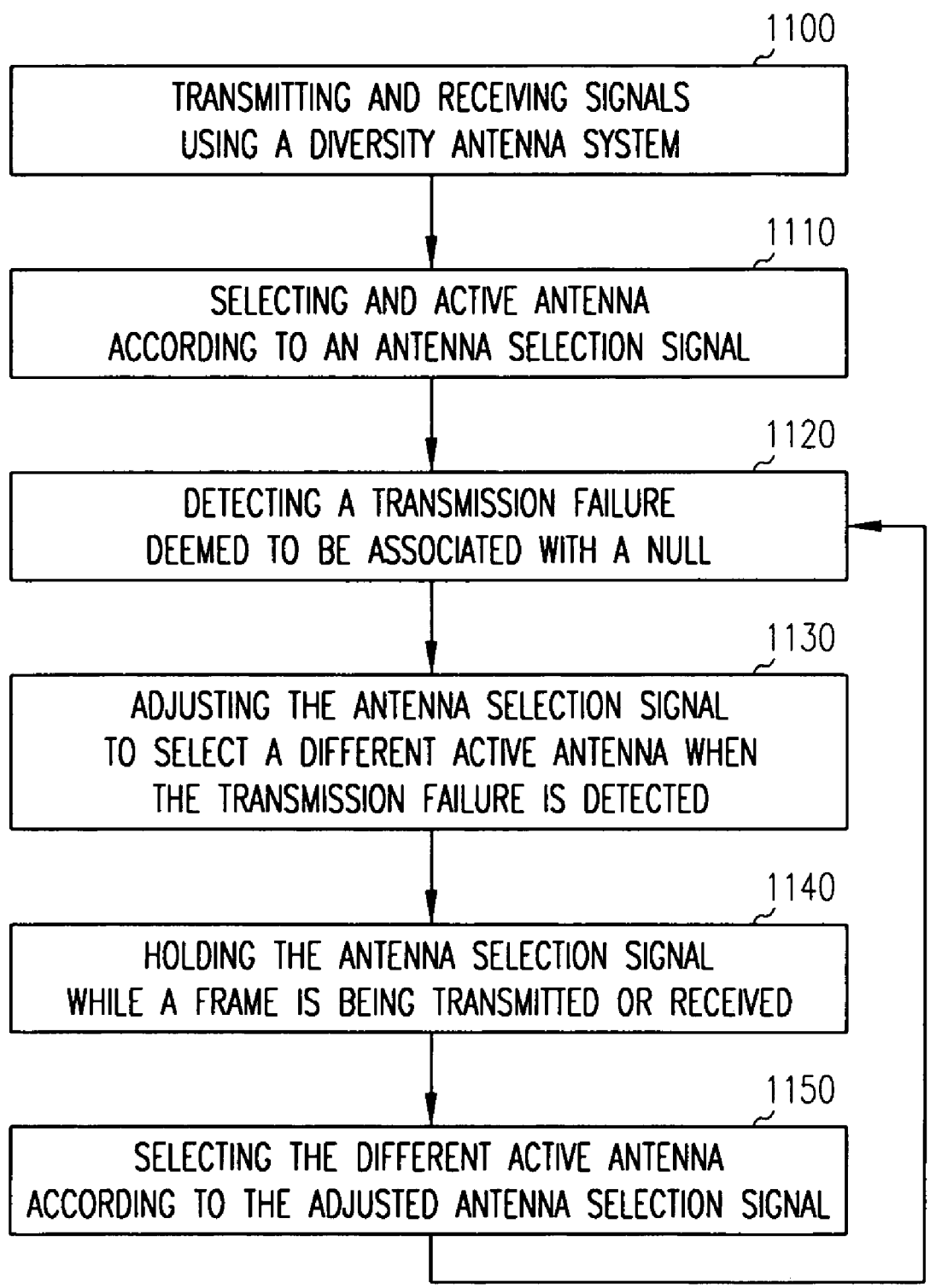
FIG. 11 is a flow chart illustrating a method for operating a telemetry system communicating with an implantable medical device.

FIG. 11 is a flow chart illustrating a method for operating a telemetry system communicating with an implantable medical device. In one embodiment, the method is performed by external telemetry system 322, including of its specific embodiments discussed in this document.

Signals are transmitted and received using a diversity antenna system including two or more antennas at 1100. This includes transmitting an outgoing signal to the implantable medical device and receiving an incoming signal from the implantable medical device. The outgoing signal includes an RF carrier signal modulated with outgoing data frames by the telemetry system communicating with the implantable medical device. The incoming signal includes another RF carrier signal modulated with incoming data frames by the implantable medical device. The incoming data frames are recovered by demodulating the received incoming signal. In one embodiment, ASK is the modulation scheme used to modulate the outgoing signal and the incoming signal.

An active antenna is selected according to an antenna selection signal at 1110. The active antenna is an antenna that is currently used for transmitting and/or receiving signals. The antenna selection signal controls which one or more antennas of the diversity antenna system are active.

A transmission failure deemed to be associated with a null is detected at 1120. The null is known to cause such a transmission failure. Examples of the transmission failure include an incoming frame failure, a response frame failure, and a signal strength failure. One or more types of such transmission failures are detected as an indication of a null by the telemetry system communicating with the implantable medical device. An incoming frame failure is detected, for example, by detecting a CRC failure or a lack of comma from the incoming signal. A response frame failure is detected, for example, by detecting a CRC failure or a lack of response frame from the incoming signal. The response frame is sent from the implantable medical device in response to an outgoing data frame sent to the implantable medical device. The lack of response frame is detected within a predetermined period after the outgoing data frame is sent to the implantable medical device. The signal strength failure is detected, for example, by detecting a sudden drop in a strength parameter, such as amplitude or power, of the outgoing signal and/or the incoming signal. The strength parameter is measured by the telemetry system communicating with the implantable medical device, by the implantable medical device, or both. In one embodiment, a transmitting antenna is selected for transmitting the outgoing signal to the implantable medical device based on the signal strength of the outgoing signal as measured and reported by the implantable medical device, and a receiving antenna is selected for receiving the incoming signal from the implantable medical device based on the signal strength of the incoming signal as measured by the telemetry system communicating with the implantable medical device.

When the transmission failure is detected, the antenna selection signal is adjusted to select a different active antenna at 1130. In other words, when a null is deemed to be encountered, the telemetry system switches from the currently used antenna to a different antenna. It is very unlikely that the null is encountered with two antennas of the telemetry system at the same time.

The antenna selection signal is held while a frame is being transmitted or received at 1140. To prevent data transmission errors, the antenna selection signal causes actual antenna switching when no data frame is being transmitted or received. This is particularly important when the time required to complete an antenna switching is not substantially shorter than the time required for transmitting or receiving a data bit. In one embodiment, an antenna switching is permitted while a data frame is being transmitted or received when the time required to complete the antenna switching is substantially shorter than the time required for transmitting or receiving a data bit. In another embodiment, an antenna switching is permitted while a data frame is being transmitted or received when an error correction algorithm is executed to correct potential data transmission errors.

The different active antenna is selected according to the adjusted antenna selection signal at 1150. This newly selected active antenna is to be used for transmitting and/or receiving data frames until another transmission failure is detected. During a telemetry session, steps 1120-1150 are repeated to continuously monitor for the transmission failures and switch to a different antenna when a transmission failure is detected.

Figure 12:
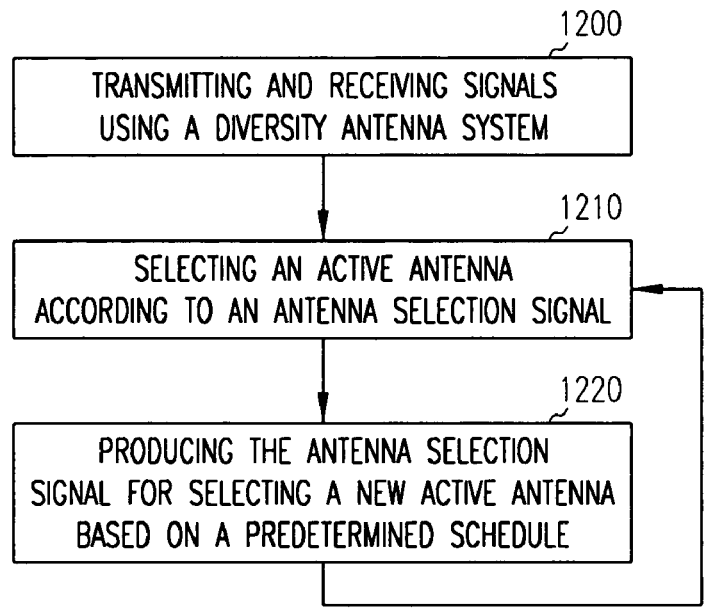
FIG. 12 is a flow chart illustrating another method for operating a telemetry system communicating with the implantable medical device.

FIG. 12 is a flow chart illustrating another method for operating a telemetry circuit communicating with the implantable medical device. In one embodiment, the method is performed by external telemetry system 922.

Signals are transmitted and received using a diversity antenna system including two or more antennas at 1200. This includes transmitting the outgoing signal to the implantable medical device and receiving the incoming signal from the implantable medical device, as discussed above for step 1100.

An active antenna is selected according to an antenna selection signal at 1210. The active antenna is an antenna that is currently used for transmitting and/or receiving antennas. The antenna selection signal controls which one or more antennas of the diversity antenna system are active.

The antenna selection signal is produced for selecting a new active antenna based on a predetermined schedule at 1220. In other words, the antenna selection signal is adjusted at times specified by the predetermined schedule. The antenna selection signal is adjusted according to an antenna selection sequence chosen to reduce or minimize the probability for the telemetry system to encounter a null. Depending on how the antenna selection sequence is generated, the new active antenna may be the same antenna that is currently used or a different antenna. In one embodiment, the new active antenna is always different from the antenna that is currently used. In one embodiment, the antenna selection signal is produced based on a dynamically generated random sequence. In an alternative embodiment, the antenna selection signal is produced based on a predetermined sequence. In one embodiment, a new active antenna is selected on a periodic basis. In a further embodiment, the antenna selection signal is held while a frame is being transmitted or received.

During a telemetry session, steps 1210-1220 are repeated to adjust the antenna selection signal at predetermined times, such as the predetermined periodic basis. The probability for the telemetry system to encounter a null is reduced because both the location of the nulls and the location of the active antenna vary while the telemetry system communicates with the implantable medical device.

Figure 13:
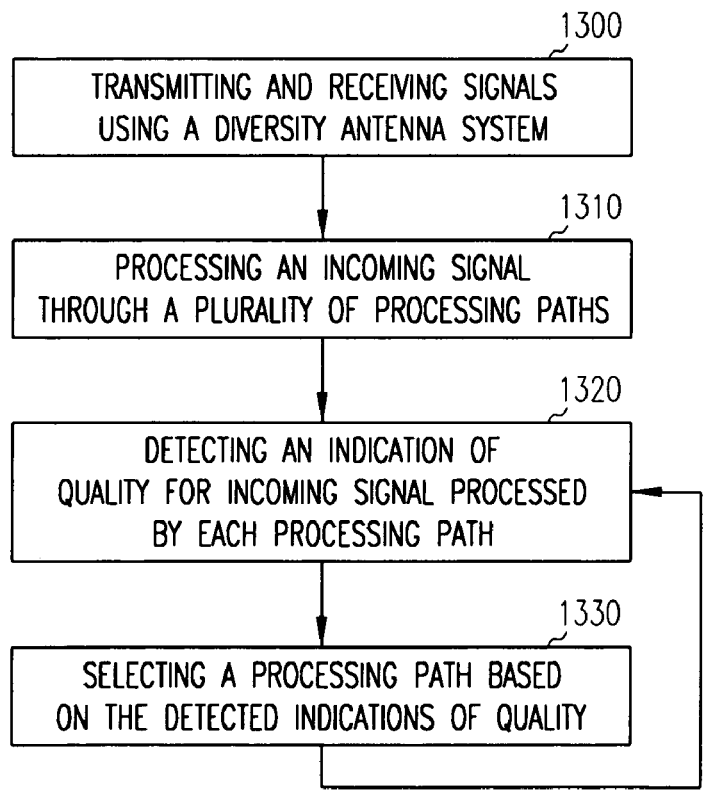
FIG. 13 is a flow chart illustrating another method for operating a telemetry system communicating with the implantable medical device.

FIG. 13 is a flow chart illustrating another method for operating a telemetry circuit communicating with the implantable medical device. In one embodiment, the method is performed by external telemetry system 1022.

Signals are transmitted and received using a diversity antenna system including two or more antennas at 1300. This includes transmitting the outgoing signal to the implantable medical device and receiving the incoming signal from the implantable medical device, as discussed above for step 1100. The two or more antennas are used to receive the incoming signal simultaneously.

The incoming signal is processed through a plurality of processing paths at 1310. In one embodiment, the plurality of processing paths each include a processing modules each coupled to one antenna of the diversity antenna system to process the incoming signal received by that antenna.

An indication of quality for the incoming signal processed by each processing path is detected at 1320. The detection results in indications of quality each associated with one of the processing paths. Examples of the indication of quality include presence of incoming frame failures and incoming signal strength failures. Such indications of quality are indicative of a possibility that the telemetry system has encountered a null. One or more types of such indications of quality are detected by the telemetry system. An incoming frame failure is detected, for example, by detecting a CRC failure or a lack of comma from the incoming signal. The incoming signal strength failure is detected, for example, by detecting a sudden drop in a strength parameter, such as amplitude or power, of the incoming signal.

A processing path is selected based on the detected indications of quality at 1330. In one embodiment, the selection becomes effective while no data frame is being transmitted or received. During a telemetry session, steps 1320-1330 are repeated to continuously monitor for the indication of quality and to switch to a different processing path when the indication of quality suggests that the telemetry system has encountered a null.

In various embodiments, the circuits described in this document are implemented by hardware, software, firmware, or any combination thereof. In various embodiments, the circuits or portions thereof described in this document are each an application-specific circuit constructed to perform one or more particular functions, a general-purpose circuit programmed to perform such function(s), or a combination thereof.

It is to be understood that the above detailed description is intended to be illustrative, and not restrictive. For example, the implantable medical device can be any implantable medical device capable of communicating with an external system or device via RF telemetry. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A system for communicating with an implantable medical device, the system comprising:
   a diversity antenna system including a plurality of antennas configured to transmit an outgoing signal to the implantable medical device and to receive an incoming signal from the implantable medical device;
   a transceiver adapted to transmit outgoing data frames by modulating the outgoing signal and to receive incoming data frames by demodulating the incoming signal, the outgoing data frames and the incoming data frames each being a unit of data including a header, a payload, and a trailer;
   an antenna interface circuit coupled between the diversity antenna system and the transceiver, the antenna interface circuit including a switch circuit adapted to connect an antenna of the diversity antenna system to the transceiver according to an antenna selection signal; and
   an antenna control circuit adapted to produce the antenna selection signal, the antenna control circuit including:
      a fading detector coupled to the transceiver, the fading detector adapted to detect a transmission failure deemed to be associated with a null, the fading detector including an incoming frame failure detector adapted to detect an incoming frame failure being a data transmission error in at least one frame of the incoming data frames, the incoming frame failure detector including a lack-of-comma detector adapted to detect a comma indicative of a receipt of a frame of the incoming data frames during a predetermined time window and to indicate the incoming frame failure if the comma is not detected during the predetermined time window;
      an antenna selector coupled to the fading detector, the antenna selector adapted to adjust the antenna selection signal for connecting a different antenna of the diversity antenna system to the transceiver in response to a detection of the transmission failure including the incoming frame failure; and
      an antenna switching timing circuit coupled between the antenna selector and the switch circuit, the antenna switching timing circuit adapted to hold the antenna selection signal such that the antenna of the diversity antenna system remains connected to the transceiver while a frame of the outgoing data frames is being transmitted or a frame of the incoming data frames is being received.

2. The system of claim 1, wherein the switch circuit is adapted to connect the antenna of the diversity antenna system to the transceiver for transmitting the outgoing signal and receiving the incoming signal.

3. The system of claim 1, wherein the incoming frame failure detector comprises a cyclic redundancy check (CRC) failure detector adapted to detect a CRC failure from the incoming data frames and to indicate the incoming frame failure when the CRC failure is detected.

4. A system for communicating with an implantable medical device, the system comprising:
   a diversity antenna system including a plurality of antennas configured to transmit an outgoing signal to the implantable medical device and to receive an incoming signal from the implantable medical device;
   a transceiver adapted to transmit outgoing data frames by modulating the outgoing signal and to receive incoming data frames by demodulating the incoming signal, the outgoing data frames and the incoming data frames each being a unit of data including a header, a payload, and a trailer;
   an antenna interface circuit coupled between the diversity antenna system and the transceiver, the antenna interface circuit including a switch circuit adapted to connect an antenna of the diversity antenna system to the transceiver according to an antenna selection signal; and
   an antenna control circuit adapted to produce the antenna selection signal, the antenna control circuit including:
      a fading detector coupled to the transceiver, the fading detector adapted to detect a transmission failure deemed to be associated with a null and including a response failure detector adapted to detect a response failure being a data transmission error in at least one response frame of the incoming data frames, the at least one response frame responding to a transmission of a frame of the outgoing data frames;
      an antenna selector coupled to the fading detector, the antenna selector adapted to adjust the antenna selection signal for connecting a different antenna of the diversity antenna system to the transceiver in response to a detection of the transmission failure including the response failure; and
      an antenna switching timing circuit coupled between the antenna selector and the switch circuit, the antenna switching timing circuit adapted to hold the antenna selection signal such that the switch circuit does not change the connection between the antenna and the transceiver while a frame of the outgoing data frames is being transmitted or a frame of the incoming data frames is being received.

5. The system of claim 4, wherein the response failure detector comprises a lack-of-response failure detector adapted to detect the at least one response frame of the incoming data frames during a predetermined time interval starting with the transmission of the frame of the outgoing data frames and to indicate the response failure if the response frame is not detected.

6. The system of claim 4, wherein the response failure detector comprises a cyclic redundancy check (CRC) failure detector adapted to detect a CRC failure in the at least one response frame of the incoming data frames following the transmission of the frame of the outgoing data frames and to indicate the response failure if the CRC failure is detected.

7. A system for communicating with an implantable medical device, the system comprising:
   a diversity antenna system including a plurality of antennas configured to transmit an outgoing signal to the implantable medical device and to receive an incoming signal from the implantable medical device;
   a transceiver adapted to transmit outgoing data frames by modulating the outgoing signal and to receive incoming data frames by demodulating the incoming signal, the outgoing data frames and the incoming data frames each being a unit of data including a header, a payload, and a trailer;

an antenna interface circuit coupled between the diversity antenna system and the transceiver, the antenna interface circuit including a switch circuit adapted to connect an antenna of the diversity antenna system to the transceiver according to an antenna selection signal; and an antenna control circuit adapted to produce the antenna selection signal, the antenna control circuit including:

a fading detector coupled to the transceiver, the fading detector adapted to detect a transmission failure deemed to be associated with a null and including a signal strength failure detector adapted to detect a signal strength failure of at least one of the incoming signal and the outgoing signal;

an antenna selector coupled to the fading detector, the antenna selector adapted to adjust the antenna selection signal for connecting a different antenna of the diversity antenna system to the transceiver in response to a detection of the transmission failure including the signal strength failure; and an antenna switching timing circuit coupled between the antenna selector and the switch circuit, the antenna switching timing circuit adapted to hold the antenna selection signal such that the switch circuit does not change the connection between the antenna and the transceiver while a frame of the outgoing data frames is being transmitted or a frame of the incoming data frames is being received.

8. The system of claim 7, wherein the signal strength failure detector comprises:

a signal strength detector to measure a strength parameter being a measure of strength of the incoming signal;

a threshold generator, coupled to the signal strength detector, to dynamically produce a threshold strength based on the measured strength parameter; and a comparator having a first input to receive the measured strength parameter, a second input to receive the dynamically produced threshold strength, and an output to indicate the signal strength failure when the measured strength parameter falls below the dynamically produced threshold strength.

9. A method for operating a telemetry system communicating with an implantable medical device, the method comprising:

transmitting an outgoing signal to the implantable medical device and receiving an incoming signal from the implantable medical device using a diversity antenna system including a plurality of antennas, wherein transmitting the outgoing signal includes transmitting outgoing data frames by modulating the outgoing signal, and receiving the incoming signal includes receiving incoming data frames by demodulating the incoming signal, the outgoing data frames and the incoming data frames each being a unit of data including a header, a payload, and a trailer;

selecting an active antenna from the diversity antenna system according to an antenna selection signal;

detecting a transmission failure deemed to be associated with a null, the transmission failure including an incoming frame failure being a data transmission error in at least one frame of the incoming data frames, wherein detecting the transmission failure comprises detecting a comma indicative of a receipt of a frame of the incoming data frames during a predetermined time window and indicating the incoming frame failure if the comma is not detected during the predetermined time window;

adjusting the antenna selection signal for selecting a different active antenna of the diversity antenna system in response to a detection of the transmission failure including the incoming frame failure;

holding the antenna selection signal such that a switching from the active antenna to the different active antenna does not occur while a frame of the outgoing data frames is being transmitted or a frame of the incoming data frames is being received; and selecting the different active antenna from the diversity antenna system according to the adjusted antenna selection signal.

10. The method of claim 9, wherein selecting the active antenna comprises selecting an antenna for receiving the incoming signal and transmitting the outgoing signal.

11. The method of claim 9, wherein detecting the transmission failure comprises cyclic comprises detecting a cyclic redundancy check (CRC) failure from the incoming data frames and indicating the incoming frame failure when the CRC failure is detected.

12. A method for operating a telemetry system communicating with an implantable medical device, the method comprising:

transmitting an outgoing signal to the implantable medical device and receiving an incoming signal from the implantable medical device using a diversity antenna system including a plurality of antennas, wherein transmitting the outgoing signal includes transmitting outgoing data frames by modulating the outgoing signal, and receiving the incoming signal includes receiving incoming data frames by demodulating the incoming signal, the outgoing data frames and the incoming data frames each being a unit of data including a header, a payload, and a trailer;

selecting an active antenna from the diversity antenna system according to an antenna selection signal;

detecting a transmission failure deemed to be associated with a null, the transmission failure including a response failure being a data transmission error in at least one response frame of the incoming data frames, the at least one response frame responding to a transmission of a frame of the outgoing data frames;

adjusting the antenna selection signal for selecting a different active antenna of the diversity antenna system in response to a detection of the transmission failure including the response failure;

holding the antenna selection signal such that the selecting the different active antenna does not occur while a frame of the outgoing data frames is being transmitted or a frame of the incoming data frames is being received; and selecting the different active antenna from the diversity antenna system according to the adjusted antenna selection signal.

13. The method of claim 12, wherein detecting the response failure comprises detecting at least one response frame of the incoming data frames during a predetermined time interval staffing with the transmission of the frame of the outgoing data frames and indicating the response failure if the response frame is not detected.

14. The method of claim 12, wherein detecting the response failure comprises detecting a cyclic redundancy check (CRC) failure detector in the at least one response frame of the incoming data frames following the transmission of the frame of the outgoing data frames and indicating the response failure if the CRC failure is detected.

15. A method for operating a telemetry system communicating with an implantable medical device, the method comprising:
  transmitting an outgoing signal to the implantable medical device and receiving an incoming signal from the implantable medical device using a diversity antenna system including a plurality of antennas, wherein transmitting the outgoing signal includes transmitting outgoing data frames by modulating the outgoing signal, and receiving the incoming signal includes receiving incoming data frames by demodulating the incoming signal, the outgoing data frames and the incoming data frames each being a unit of data including a header, a payload, and a trailer;
  selecting an active antenna from the diversity antenna system according to an antenna selection signal;
  detecting a transmission failure deemed to be associated with a null, the transmission failure including a signal strength failure of at least one of the incoming signal and the outgoing signal;
  adjusting the antenna selection signal for selecting a different active antenna of the diversity antenna system in response to a detection of the transmission failure including the signal strength failure;
  holding the antenna selection signal such that the selecting the different active antenna does not occur while a frame of the outgoing data frames is being transmitted or a frame of the incoming data frames is being received; and
  selecting the different active antenna from the diversity antenna system according to the adjusted antenna selection signal.

16. The method of claim 15, wherein detecting the signal strength failure comprises:
  measuring a strength parameter being a measure of strength of the incoming signal;
  producing a threshold strength dynamically based on the measured strength parameter; and
  indicating the signal strength failure when the measured strength parameter falls below the dynamically produced threshold strength.

17. A system for communicating with an implantable medical device, the system comprising:
  a diversity antenna system including a plurality of antennas configured to transmit an outgoing signal to the implantable medical device and to receive an incoming signal from the implantable medical device;
  an external system controller;
  a transceiver adapted to transmit outgoing data frames by modulating the outgoing signal and to receive incoming data frames by demodulating the incoming signal, the transceiver including:
    a plurality of receiving modules each having an input coupled to one antenna of the diversity antenna system and an output; and
    a switch circuit to connect the output of one receiving module of the plurality of receiving modules to the external system controller according to a receiving path selection signal; and
  an antenna control circuit adapted to produce the receiving path selection signal, the antenna control circuit including:
    a signal quality assessment circuit coupled to the transceiver, the signal quality assessment circuit adapted to produce an indication of quality for the incoming signal processed by each receiving module of the plurality of receiving modules;
    a receiving path selector coupled to the transceiver, the receiving path selector adapted to adjust the receiving path selection signal based on the indications of quality for the incoming signal produced for the plurality of receiving modules; and
    a path switching timing circuit coupled between the receiving path selector and the switch circuit, the path switching timing circuit adapted to hold the receiving path selection signal while a frame of the outgoing data frames is being transmitted or a frame of the incoming data frames is being received.

18. The system of claim 17, wherein the signal quality assessment circuit comprises an incoming frame failure detector adapted to detect an incoming frame failure from the incoming signal processed by each receiving module of the plurality of receiving modules, and the receiving path selector is adapted to deselect a receiving module of the plurality of receiving modules when the incoming frame failure is indicated for that receiving module.

19. The system of claim 18, wherein the incoming frame failure detector comprises a cyclic redundancy check (CRC) failure detector adapted to detect a CRC failure from the incoming signal processed by each receiving module of the plurality of receiving modules and to indicate the incoming frame failure for the each receiving module when the CRC failure is detected.

20. The system of claim 18, wherein the incoming frame failure detector comprises a lack-of-comma detector adapted to detect a comma indicative of a data frame from the incoming signal processed by each receiving module of the plurality of receiving modules during a predetermined time window and to indicate the response failure for the each receiving module if the comma is not detected during the predetermined time window.

21. The system of claim 17, wherein the signal quality assessment circuit comprises a signal strength detector adapted to measure a strength parameter being a measure of strength of the incoming signal processed by each receiving module of the plurality of receiving modules.

22. The system of claim 21, wherein the receiving path selector is adapted to adjust the receiving path selection signal based on the measured strength parameters for the plurality of receiving modules.

23. The system of claim 22, wherein the signal strength detector comprises an incoming signal strength failure detector adapted to detect an incoming signal strength failure associated with the incoming signal processed by each receiving module of the plurality of receiving modules, and wherein the receiving path selector is adapted deselect a receiving module of the plurality of receiving modules when the incoming signal strength failure is indicated for that receiving module.

24. The system of claim 17, wherein the outgoing signal and the incoming signal are each modulated by amplitude-shift-keying (ASK), and the transceiver comprises an ASK modulator to modulate the outgoing signal with the outgoing data frames and an ASK demodulator to recover the incoming data frames by demodulating the incoming signal.

25. A method for operating a telemetry system communicating with an implantable medical device, the method comprising:
  transmitting an outgoing signal to the implantable medical device and receiving an incoming signal from the implantable medical device using a diversity antenna system including a plurality of antennas, wherein transmitting the outgoing signal includes transmitting outgoing data frames by modulating the outgoing signal, and receiving the incoming signal includes receiving incoming data frames by demodulating the incoming signal;

processing the incoming signal through a plurality of processing paths each coupled to one antenna of the diversity antenna system;

detecting an indication of quality for the incoming signal processed by each processing path of the plurality of processing paths; and selecting a processing path of the plurality of processing paths based on the detected indications of quality associated with the plurality of processing paths, the processing path selected while a frame of the outgoing data frames is not being transmitted and a frame of the incoming data frames is not being received.

26. The method of claim 25, wherein detecting the indication of quality comprises detecting an incoming frame failure in each processing path of the plurality of processing paths, and selecting the processing path comprises selecting a processing path in which the incoming frame failure is not detected.

27. The method of claim 26, wherein detecting the incoming frame failure comprises detecting a cyclic redundancy check (CRC) failure.

28. The method of claim 27, wherein detecting the incoming frame failure comprises detecting a lack of comma indicative of an incoming data frame of the incoming data frames.

29. The method of claim 25, wherein detecting the indication of quality comprises measuring a strength parameter being a measure of strength of the incoming signal processed by each processing path of the plurality of processing paths.

30. The method of claim 29, wherein selecting the processing path comprises selecting the processing path of the plurality of processing paths based on the measured strength parameters for the plurality of processing paths.

31. The method of claim 30, wherein measuring the strength parameter comprises detecting an incoming signal strength failure associated with the incoming signal processed by each processing path of the plurality of processing paths, and selecting the processing path comprises selecting a processing path in which the incoming signal strength failure is not detected.

32. The method of claim 25, further comprising modulating each of the outgoing signal and the incoming signal by amplitude-shift-keying (ASK).

* * * * *

UNITED STATES PATENT AND TRADEMARK OFFICE
CERTIFICATE OF CORRECTION

PATENT NO. : 7,610,065 B2  Page 1 of 1
APPLICATION NO. : 11/068478
DATED : October 27, 2009
INVENTOR(S) : Vineel Vallapureddy et al.

It is certified that error appears in the above-identified patent and that said Letters Patent is hereby corrected as shown below:

In column 20, line 59, in Claim 13, delete "staffing" and insert -- starting --, therefor.

Signed and Sealed this

Twenty-sixth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,610,065 B2 | Page 1 of 1 |
| APPLICATION NO. | : 11/068478 | |
| DATED | : October 27, 2009 | |
| INVENTOR(S) | : Vallapureddy et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 781 days.

Signed and Sealed this

Twelfth Day of October, 2010

David J. Kappos
*Director of the United States Patent and Trademark Office*